(12) United States Patent
Long

(10) Patent No.: US 11,589,919 B2
(45) Date of Patent: Feb. 28, 2023

(54) APPARATUS AND METHODS FOR RENAL DENERVATION ABLATION

(71) Applicant: Farapulse, Inc., Menlo Park, CA (US)

(72) Inventor: Gary Long, Cincinnati, OH (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 420 days.

(21) Appl. No.: 16/719,708

(22) Filed: Dec. 18, 2019

(65) Prior Publication Data
US 2020/0297411 A1     Sep. 24, 2020

Related U.S. Application Data

(60) Division of application No. 15/201,997, filed on Jul. 5, 2016, now Pat. No. 10,517,672, which is a
(Continued)

(51) Int. Cl.
| A61B 18/12 | (2006.01) |
| A61B 18/14 | (2006.01) |
| A61B 18/00 | (2006.01) |

(52) U.S. Cl.
CPC ...... *A61B 18/1492* (2013.01); *A61B 18/1206* (2013.01); *A61B 2018/00285* (2013.01);
(Continued)

(58) Field of Classification Search
CPC ............ A61B 18/1206; A61B 18/1492; A61B 2018/00577; A61B 2018/00875;
(Continued)

(56) References Cited

U.S. PATENT DOCUMENTS

| 4,200,104 A | 4/1980 | Harris |
| 4,470,407 A | 9/1984 | Hussein |

(Continued)

FOREIGN PATENT DOCUMENTS

| EP | 1125549 | 8/2001 |
| EP | 0797956 | 6/2003 |

(Continued)

OTHER PUBLICATIONS

Office Action for Canadian Application No. 2,881,462, dated Mar. 19, 2019, 5 pages.
(Continued)

*Primary Examiner* — Daniel W Fowler
(74) *Attorney, Agent, or Firm* — Nelson Mullins Riley & Scarborough LLP

(57) ABSTRACT

A catheter device for renal denervation ablation includes a flexible catheter shaft having an electrically insulating expandable member in its distal portion with at least one electrode located proximal to the member, at least one electrode located distal to the member, and with openings in the distal shaft with at least one opening proximal to the proximal electrode and one opening distal to the distal electrode of said electrode pair, said openings connected through an inner lumen in the catheter that provides a path for blood to flow through the expandable member. In one embodiment, the device comprises a flexible catheter shaft with a multiplicity of recessed paired electrodes disposed in recessed spaces in its distal portion, such that an electrically conducting portion of each electrode is exposed to the exterior of the catheter within a recessed space, and with an electrical insulator separating the electrodes of each pair.

13 Claims, 22 Drawing Sheets

Related U.S. Application Data continuation of application No. PCT/US2015/010223, filed on Jan. 6, 2015.

(60) Provisional application No. 61/923,966, filed on Jan. 6, 2014, provisional application No. 61/923,969, filed on Jan. 6, 2014.

(52) U.S. Cl.
CPC ............... *A61B 2018/00404* (2013.01); *A61B 2018/00434* (2013.01); *A61B 2018/00511* (2013.01); *A61B 2018/00577* (2013.01); *A61B 2018/00613* (2013.01); *A61B 2018/00875* (2013.01); *A61B 2018/128* (2013.01); *A61B 2018/1266* (2013.01); *A61B 2018/1467* (2013.01)

(58) Field of Classification Search
CPC ...... A61B 2018/1266; A61B 2018/128; A61B 2018/1467
See application file for complete search history.

(56) References Cited

U.S. PATENT DOCUMENTS

| | | |
|---|---|---|
| 5,242,441 A | 9/1993 | Avitall |
| 5,257,635 A | 11/1993 | Langberg |
| 5,281,213 A | 1/1994 | Milder et al. |
| 5,334,193 A | 8/1994 | Nardella |
| 5,341,807 A | 8/1994 | Nardella |
| 5,342,301 A | 8/1994 | Saab |
| 5,398,683 A | 3/1995 | Edwards et al. |
| 5,443,463 A | 8/1995 | Stern et al. |
| 5,454,370 A | 10/1995 | Avitall |
| 5,515,848 A | 5/1996 | Corbett, III et al. |
| 5,531,685 A | 7/1996 | Hemmer et al. |
| 5,545,161 A | 8/1996 | Imran |
| 5,578,040 A | 11/1996 | Smith |
| 5,617,854 A | 4/1997 | Munsif |
| 5,624,430 A | 4/1997 | Eton et al. |
| 5,667,491 A | 9/1997 | Pliquett et al. |
| 5,672,170 A | 9/1997 | Cho |
| 5,700,243 A | 12/1997 | Narciso, Jr. |
| 5,702,438 A | 12/1997 | Avitall |
| 5,706,823 A | 1/1998 | Wodlinger |
| 5,722,400 A | 3/1998 | Ockuly et al. |
| 5,722,402 A | 3/1998 | Swanson et al. |
| 5,749,914 A | 5/1998 | Janssen |
| 5,779,699 A | 7/1998 | Lipson |
| 5,788,692 A | 8/1998 | Campbell et al. |
| 5,810,762 A | 9/1998 | Hofmann |
| 5,833,710 A | 11/1998 | Jacobson |
| 5,836,874 A | 11/1998 | Swanson et al. |
| 5,836,942 A | 11/1998 | Netherly et al. |
| 5,836,947 A | 11/1998 | Fleischman et al. |
| 5,843,154 A | 12/1998 | Osypka |
| 5,849,028 A | 12/1998 | Chen |
| 5,863,291 A | 1/1999 | Schaer |
| 5,868,736 A | 2/1999 | Swanson et al. |
| 5,871,523 A | 2/1999 | Fleischman et al. |
| 5,876,336 A | 3/1999 | Swanson et al. |
| 5,895,404 A | 4/1999 | Ruiz |
| 5,899,917 A | 5/1999 | Edwards et al. |
| 5,904,709 A | 5/1999 | Arndt et al. |
| 5,916,158 A | 6/1999 | Webster, Jr. |
| 5,916,213 A | 6/1999 | Haissaguerre et al. |
| 5,921,924 A | 7/1999 | Avitall |
| 5,928,269 A | 7/1999 | Alt |
| 5,928,270 A | 7/1999 | Ramsey, III |
| 6,002,955 A | 12/1999 | Willems et al. |
| 6,006,131 A | 12/1999 | Cooper et al. |
| 6,009,351 A | 12/1999 | Flachman |
| 6,014,579 A | 1/2000 | Pomeranz et al. |
| 6,029,671 A | 2/2000 | Stevens et al. |
| 6,033,403 A | 3/2000 | Tu et al. |
| 6,045,550 A | 4/2000 | Simpson et al. |
| 6,068,653 A | 5/2000 | LaFontaine |
| 6,071,274 A | 6/2000 | Thompson et al. |
| 6,071,281 A | 6/2000 | Burnside et al. |
| 6,090,104 A | 7/2000 | Webster, Jr. |
| 6,096,036 A | 8/2000 | Bowe et al. |
| 6,113,595 A | 9/2000 | Muntermann |
| 6,119,041 A | 9/2000 | Pomeranz et al. |
| 6,120,500 A | 9/2000 | Bednarek et al. |
| 6,146,381 A | 11/2000 | Bowe et al. |
| 6,164,283 A | 12/2000 | Lesh |
| 6,167,291 A | 12/2000 | Barajas et al. |
| 6,216,034 B1 | 4/2001 | Hofmann et al. |
| 6,219,582 B1 | 4/2001 | Hofstad et al. |
| 6,223,085 B1 | 4/2001 | Dann et al. |
| 6,231,518 B1 | 5/2001 | Grabek et al. |
| 6,245,064 B1 | 6/2001 | Lesh et al. |
| 6,251,107 B1 | 6/2001 | Schaer |
| 6,251,128 B1 | 6/2001 | Knopp et al. |
| 6,270,476 B1 | 8/2001 | Santoianni et al. |
| 6,272,384 B1 | 8/2001 | Simon et al. |
| 6,287,306 B1 | 9/2001 | Kroll et al. |
| 6,314,963 B1 | 11/2001 | Vaska et al. |
| 6,322,559 B1 | 11/2001 | Daulton et al. |
| 6,350,263 B1 | 2/2002 | Wetzig et al. |
| 6,370,412 B1 | 4/2002 | Armoundas et al. |
| 6,391,024 B1 | 5/2002 | Sun et al. |
| 6,447,505 B2 | 9/2002 | McGovern et al. |
| 6,464,699 B1 | 10/2002 | Swanson |
| 6,470,211 B1 | 10/2002 | Ideker et al. |
| 6,502,576 B1 | 1/2003 | Lesh |
| 6,503,247 B2 | 1/2003 | Swartz et al. |
| 6,517,534 B1 | 2/2003 | McGovern et al. |
| 6,527,724 B1 | 3/2003 | Fenici |
| 6,527,767 B2 | 3/2003 | Wang et al. |
| 6,592,581 B2 | 7/2003 | Bowe |
| 6,595,991 B2 | 7/2003 | Tollner et al. |
| 6,607,520 B2 | 8/2003 | Keane |
| 6,623,480 B1 | 9/2003 | Kuo et al. |
| 6,638,278 B2 | 10/2003 | Falwell et al. |
| 6,666,863 B2 | 12/2003 | Wentzel et al. |
| 6,669,693 B2 | 12/2003 | Friedman |
| 6,702,811 B2 | 3/2004 | Stewart et al. |
| 6,719,756 B1 | 4/2004 | Muntermann |
| 6,723,092 B2 | 4/2004 | Brown et al. |
| 6,728,563 B2 | 4/2004 | Rashidi |
| 6,743,225 B2 | 6/2004 | Sanchez et al. |
| 6,743,239 B1 | 6/2004 | Kuehn et al. |
| 6,764,486 B2 | 7/2004 | Natale |
| 6,780,181 B2 | 8/2004 | Kroll et al. |
| 6,805,128 B1 | 10/2004 | Pless |
| 6,807,447 B2 | 10/2004 | Griffin, III |
| 6,892,091 B1 | 5/2005 | Ben-Haim et al. |
| 6,893,438 B2 | 5/2005 | Hall et al. |
| 6,926,714 B1 | 8/2005 | Sra |
| 6,955,173 B2 | 10/2005 | Lesh |
| 6,960,206 B2 | 11/2005 | Keane |
| 6,960,207 B2 | 11/2005 | Vanney et al. |
| 6,972,016 B2 | 12/2005 | Hill, III et al. |
| 6,973,339 B2 | 12/2005 | Govari |
| 6,979,331 B2 | 12/2005 | Hintringer et al. |
| 6,984,232 B2 | 1/2006 | Vanney et al. |
| 6,985,776 B2 | 1/2006 | Kane et al. |
| 7,001,383 B2 | 2/2006 | Keidar |
| 7,041,095 B2 | 5/2006 | Wang et al. |
| 7,171,263 B2 | 1/2007 | Darvish et al. |
| 7,182,725 B2 | 2/2007 | Bonan et al. |
| 7,195,628 B2 | 3/2007 | Falkenberg |
| 7,207,988 B2 | 4/2007 | Leckrone et al. |
| 7,207,989 B2 | 4/2007 | Pike, Jr. et al. |
| 7,229,402 B2 | 6/2007 | Diaz et al. |
| 7,229,437 B2 | 6/2007 | Johnson et al. |
| 7,250,049 B2 | 7/2007 | Roop et al. |
| 7,285,116 B2 | 10/2007 | de la Rama et al. |
| 7,285,119 B2 | 10/2007 | Stewart et al. |
| 7,326,208 B2 | 2/2008 | Vanney et al. |
| 7,346,379 B2 | 3/2008 | Eng et al. |
| 7,367,974 B2 | 5/2008 | Haemmerich et al. |

(56) References Cited

U.S. PATENT DOCUMENTS

| | | |
|---|---|---|
| 7,374,567 B2 | 5/2008 | Heuser |
| 7,387,629 B2 | 6/2008 | Vanney et al. |
| 7,387,630 B2 | 6/2008 | Mest |
| 7,387,636 B2 | 6/2008 | Cohn et al. |
| 7,416,552 B2 | 8/2008 | Paul et al. |
| 7,419,477 B2 | 9/2008 | Simpson et al. |
| 7,419,489 B2 | 9/2008 | Vanney et al. |
| 7,429,261 B2 | 9/2008 | Kunis et al. |
| 7,435,248 B2 | 10/2008 | Taimisto et al. |
| 7,513,896 B2 | 4/2009 | Orszulak |
| 7,527,625 B2 | 5/2009 | Knight et al. |
| 7,578,816 B2 | 8/2009 | Boveja et al. |
| 7,588,567 B2 | 9/2009 | Boveja et al. |
| 7,623,899 B2 | 11/2009 | Worley et al. |
| 7,678,108 B2 | 3/2010 | Chrisitian et al. |
| 7,681,579 B2 | 3/2010 | Schwartz |
| 7,771,421 B2 | 8/2010 | Stewart et al. |
| 7,805,182 B2 | 9/2010 | Weese et al. |
| 7,850,642 B2 | 12/2010 | Moll et al. |
| 7,850,685 B2 | 12/2010 | Kunis et al. |
| 7,857,808 B2 | 12/2010 | Oral et al. |
| 7,857,809 B2 | 12/2010 | Drysen |
| 7,869,865 B2 | 1/2011 | Govari et al. |
| 7,896,873 B2 | 3/2011 | Hiller et al. |
| 7,917,211 B2 | 3/2011 | Zacouto |
| 7,918,819 B2 | 4/2011 | Karmarkar et al. |
| 7,918,850 B2 | 4/2011 | Govari et al. |
| 7,922,714 B2 | 4/2011 | Stevens-Wright |
| 7,955,827 B2 | 6/2011 | Rubinsky et al. |
| 8,048,067 B2 | 11/2011 | Davalos et al. |
| 8,048,072 B2 | 11/2011 | Verin et al. |
| 8,100,895 B2 | 1/2012 | Panos et al. |
| 8,100,900 B2 | 1/2012 | Prinz et al. |
| 8,108,069 B2 | 1/2012 | Stahler et al. |
| 8,133,220 B2 | 3/2012 | Lee et al. |
| 8,137,342 B2 | 3/2012 | Crossman |
| 8,145,289 B2 | 3/2012 | Calabro' et al. |
| 8,147,486 B2 | 4/2012 | Honour et al. |
| 8,160,690 B2 | 4/2012 | Wilfley et al. |
| 8,175,680 B2 | 5/2012 | Panescu |
| 8,182,477 B2 | 5/2012 | Orszulak et al. |
| 8,206,384 B2 | 6/2012 | Falwell et al. |
| 8,206,385 B2 | 6/2012 | Stangenes et al. |
| 8,216,221 B2 | 7/2012 | Ibrahim et al. |
| 8,221,411 B2 | 7/2012 | Francischelli et al. |
| 8,226,648 B2 | 7/2012 | Paul et al. |
| 8,228,065 B2 | 7/2012 | Wirtz et al. |
| 8,235,986 B2 | 8/2012 | Kulesa et al. |
| 8,235,988 B2 | 8/2012 | Davis et al. |
| 8,251,986 B2 | 8/2012 | Chornenky et al. |
| 8,282,631 B2 | 10/2012 | Davalos et al. |
| 8,287,532 B2 | 10/2012 | Carroll et al. |
| 8,414,508 B2 | 4/2013 | Thapliyal et al. |
| 8,430,875 B2 | 4/2013 | Ibrahim et al. |
| 8,433,394 B2 | 4/2013 | Harlev et al. |
| 8,449,535 B2 | 5/2013 | Deno et al. |
| 8,454,594 B2 | 6/2013 | Demarais et al. |
| 8,463,368 B2 | 6/2013 | Harlev et al. |
| 8,475,450 B2 | 7/2013 | Govari et al. |
| 8,486,063 B2 | 7/2013 | Werneth et al. |
| 8,500,733 B2 | 8/2013 | Watson |
| 8,535,304 B2 | 9/2013 | Sklar et al. |
| 8,538,501 B2 | 9/2013 | Venkatachalam et al. |
| 8,562,588 B2 | 10/2013 | Hobbs et al. |
| 8,568,406 B2 | 10/2013 | Harlev et al. |
| 8,571,635 B2 | 10/2013 | McGee |
| 8,571,647 B2 | 10/2013 | Harlev et al. |
| 8,585,695 B2 | 11/2013 | Shih |
| 8,588,885 B2 | 11/2013 | Hall et al. |
| 8,597,288 B2 | 12/2013 | Christian |
| 8,608,735 B2 | 12/2013 | Govari et al. |
| 8,628,522 B2 | 1/2014 | Ibrahim et al. |
| 8,632,534 B2 | 1/2014 | Pearson et al. |
| 8,647,338 B2 | 2/2014 | Chornenky et al. |
| 8,708,952 B2 | 4/2014 | Cohen et al. |
| 8,734,442 B2 | 5/2014 | Cao et al. |
| 8,771,267 B2 | 7/2014 | Kunis et al. |
| 8,795,310 B2 | 8/2014 | Fung et al. |
| 8,808,273 B2 | 8/2014 | Caples et al. |
| 8,834,461 B2 | 9/2014 | Werneth et al. |
| 8,834,464 B2 | 9/2014 | Stewart et al. |
| 8,868,169 B2 | 10/2014 | Narayan et al. |
| 8,876,817 B2 | 11/2014 | Avitall et al. |
| 8,886,309 B2 | 11/2014 | Luther et al. |
| 8,903,488 B2 | 12/2014 | Callas et al. |
| 8,920,411 B2 | 12/2014 | Gelbart et al. |
| 8,926,589 B2 | 1/2015 | Govari |
| 8,932,287 B2 | 1/2015 | Gelbart et al. |
| 8,945,117 B2 | 2/2015 | Bencini |
| 8,979,841 B2 | 3/2015 | Kunis et al. |
| 8,986,278 B2 | 3/2015 | Fung et al. |
| 9,002,442 B2 | 4/2015 | Harley et al. |
| 9,005,189 B2 | 4/2015 | Davalos et al. |
| 9,005,194 B2 | 4/2015 | Oral et al. |
| 9,011,425 B2 | 4/2015 | Fischer et al. |
| 9,044,245 B2 | 6/2015 | Condie et al. |
| 9,055,959 B2 | 6/2015 | Vaska et al. |
| 9,072,518 B2 | 7/2015 | Swanson |
| 9,078,667 B2 | 7/2015 | Besser et al. |
| 9,101,374 B1 | 8/2015 | Hoch et al. |
| 9,119,533 B2 | 9/2015 | Ghaffari |
| 9,119,634 B2 | 9/2015 | Gelbart et al. |
| 9,131,897 B2 | 9/2015 | Harada et al. |
| 9,155,590 B2 | 10/2015 | Mathur |
| 9,162,037 B2 | 10/2015 | Belson et al. |
| 9,179,972 B2 | 11/2015 | Olson |
| 9,186,481 B2 | 11/2015 | Avitall et al. |
| 9,192,769 B2 | 11/2015 | Donofrio et al. |
| 9,211,405 B2 | 12/2015 | Mahapatra et al. |
| 9,216,055 B2 | 12/2015 | Spence et al. |
| 9,233,248 B2 | 1/2016 | Luther et al. |
| 9,237,926 B2 | 1/2016 | Nollert et al. |
| 9,262,252 B2 | 2/2016 | Kirkpatrick et al. |
| 9,277,957 B2 | 3/2016 | Long et al. |
| 9,282,910 B2 | 3/2016 | Narayan et al. |
| 9,289,258 B2 | 3/2016 | Cohen |
| 9,289,606 B2 | 3/2016 | Paul et al. |
| 9,295,516 B2 | 3/2016 | Pearson et al. |
| 9,301,801 B2 | 4/2016 | Scheib |
| 9,375,268 B2 | 6/2016 | Long |
| 9,414,881 B2 | 8/2016 | Callas et al. |
| 9,468,495 B2 | 10/2016 | Kunis et al. |
| 9,474,486 B2 | 10/2016 | Eliason et al. |
| 9,474,574 B2 | 10/2016 | Ibrahim et al. |
| 9,480,525 B2 | 11/2016 | Lopes et al. |
| 9,486,272 B2 | 11/2016 | Bonyak et al. |
| 9,486,273 B2 | 11/2016 | Lopes et al. |
| 9,492,227 B2 | 11/2016 | Lopes et al. |
| 9,492,228 B2 | 11/2016 | Lopes et al. |
| 9,517,103 B2 | 12/2016 | Panescu et al. |
| 9,526,573 B2 | 12/2016 | Lopes et al. |
| 9,532,831 B2 | 1/2017 | Reinders et al. |
| 9,539,010 B2 | 1/2017 | Gagner et al. |
| 9,554,848 B2 | 1/2017 | Stewart et al. |
| 9,554,851 B2 | 1/2017 | Sklar et al. |
| 9,700,368 B2 | 7/2017 | Callas et al. |
| 9,724,170 B2 | 8/2017 | Mickelsen |
| 9,757,193 B2 | 9/2017 | Zarins et al. |
| 9,782,099 B2 | 10/2017 | Williams et al. |
| 9,795,442 B2 | 10/2017 | Salahieh et al. |
| 9,861,802 B2 | 1/2018 | Mickelsen |
| 9,913,685 B2 | 3/2018 | Clark et al. |
| 9,931,487 B2 | 4/2018 | Quinn et al. |
| 9,987,081 B1 | 6/2018 | Bowers et al. |
| 9,999,465 B2 | 6/2018 | Long et al. |
| 10,016,232 B1 | 7/2018 | Bowers et al. |
| 10,130,423 B1 | 11/2018 | Viswanathan et al. |
| 10,172,673 B2 | 1/2019 | Viswanathan et al. |
| 10,507,302 B2 | 12/2019 | Leeflang et al. |
| 10,512,505 B2 | 12/2019 | Viswanathan |
| 10,512,779 B2 | 12/2019 | Viswanathan et al. |
| 10,517,672 B2 | 12/2019 | Long |
| 2001/0000791 A1 | 5/2001 | Suorsa et al. |
| 2001/0007070 A1 | 7/2001 | Stewart et al. |

(56) References Cited

U.S. PATENT DOCUMENTS

| | | |
|---|---|---|
| 2001/0044624 A1 | 11/2001 | Seraj et al. |
| 2002/0052602 A1 | 5/2002 | Wang et al. |
| 2002/0077627 A1 | 6/2002 | Johnson et al. |
| 2002/0091384 A1 | 7/2002 | Hooven et al. |
| 2002/0111618 A1 | 8/2002 | Stewart et al. |
| 2002/0161323 A1 | 10/2002 | Miller et al. |
| 2002/0169445 A1 | 11/2002 | Jain et al. |
| 2002/0177765 A1 | 11/2002 | Bowe et al. |
| 2002/0183638 A1 | 12/2002 | Swanson |
| 2003/0014098 A1 | 1/2003 | Quijano et al. |
| 2003/0018374 A1 | 1/2003 | Paulos |
| 2003/0028189 A1 | 2/2003 | Woloszko et al. |
| 2003/0050637 A1 | 3/2003 | Maguire et al. |
| 2003/0114849 A1 | 6/2003 | Ryan |
| 2003/0125729 A1 | 7/2003 | Hooven et al. |
| 2003/0130598 A1 | 7/2003 | Manning et al. |
| 2003/0130711 A1 | 7/2003 | Pearson et al. |
| 2003/0204161 A1 | 10/2003 | Ferek Petric |
| 2003/0229379 A1 | 12/2003 | Ramsey |
| 2004/0039382 A1 | 2/2004 | Kroll et al. |
| 2004/0049181 A1 | 3/2004 | Stewart et al. |
| 2004/0049182 A1 | 3/2004 | Koblish et al. |
| 2004/0082859 A1 | 4/2004 | Schaer |
| 2004/0082948 A1 | 4/2004 | Stewart et al. |
| 2004/0087939 A1 | 5/2004 | Eggers et al. |
| 2004/0111087 A1 | 6/2004 | Stern et al. |
| 2004/0193152 A1* | 9/2004 | Sutton .................. A61B 18/18 606/50 |
| 2004/0199157 A1 | 10/2004 | Palanker et al. |
| 2004/0231683 A1 | 11/2004 | Eng et al. |
| 2004/0236360 A1 | 11/2004 | Cohn et al. |
| 2004/0254607 A1 | 12/2004 | Wittenberger et al. |
| 2004/0267337 A1 | 12/2004 | Hayzelden |
| 2005/0033282 A1 | 2/2005 | Hooven |
| 2005/0222632 A1 | 10/2005 | Obino |
| 2005/0251130 A1 | 11/2005 | Boveja et al. |
| 2005/0261672 A1 | 11/2005 | Deem et al. |
| 2006/0009755 A1 | 1/2006 | Sra |
| 2006/0009759 A1 | 1/2006 | Chrisitian et al. |
| 2006/0015095 A1 | 1/2006 | Desinger et al. |
| 2006/0015165 A1 | 1/2006 | Bertolero et al. |
| 2006/0024359 A1 | 2/2006 | Walker et al. |
| 2006/0058781 A1 | 3/2006 | Long |
| 2006/0111702 A1 | 5/2006 | Oral et al. |
| 2006/0142801 A1 | 6/2006 | Demarais et al. |
| 2006/0167448 A1 | 7/2006 | Kozel |
| 2006/0217703 A1 | 9/2006 | Chornenky et al. |
| 2006/0241734 A1 | 10/2006 | Marshall et al. |
| 2006/0264752 A1 | 11/2006 | Rubinsky et al. |
| 2006/0270900 A1 | 11/2006 | Chin et al. |
| 2006/0287648 A1 | 12/2006 | Schwartz |
| 2006/0293730 A1 | 12/2006 | Rubinsky et al. |
| 2006/0293731 A1 | 12/2006 | Rubinsky et al. |
| 2007/0005053 A1 | 1/2007 | Dando |
| 2007/0021744 A1 | 1/2007 | Creighton |
| 2007/0066972 A1 | 3/2007 | Ormsby et al. |
| 2007/0129721 A1 | 6/2007 | Phan et al. |
| 2007/0129760 A1 | 6/2007 | Demarais et al. |
| 2007/0156135 A1 | 7/2007 | Rubinsky et al. |
| 2007/0167740 A1 | 7/2007 | Grunewald et al. |
| 2007/0167940 A1 | 7/2007 | Stevens-Wright |
| 2007/0173878 A1 | 7/2007 | Heuser |
| 2007/0208329 A1 | 9/2007 | Ward et al. |
| 2007/0225589 A1 | 9/2007 | Viswanathan |
| 2007/0249923 A1 | 10/2007 | Keenan |
| 2007/0260223 A1 | 11/2007 | Scheibe et al. |
| 2007/0270792 A1 | 11/2007 | Hennemann et al. |
| 2008/0009855 A1 | 1/2008 | Hamou |
| 2008/0033426 A1 | 2/2008 | Machell |
| 2008/0065061 A1 | 3/2008 | Viswanathan |
| 2008/0086120 A1 | 4/2008 | Mirza et al. |
| 2008/0091195 A1 | 4/2008 | Silwa et al. |
| 2008/0103545 A1 | 5/2008 | Bolea et al. |
| 2008/0132885 A1 | 6/2008 | Rubinsky et al. |
| 2008/0161789 A1 | 7/2008 | Thao et al. |
| 2008/0172048 A1 | 7/2008 | Martin et al. |
| 2008/0200913 A1 | 8/2008 | Viswanathan |
| 2008/0208118 A1 | 8/2008 | Goldman |
| 2008/0243214 A1 | 10/2008 | Koblish |
| 2008/0281322 A1 | 11/2008 | Sherman et al. |
| 2008/0300574 A1 | 12/2008 | Belson et al. |
| 2008/0300588 A1 | 12/2008 | Groth et al. |
| 2009/0024084 A1 | 1/2009 | Khosla et al. |
| 2009/0048591 A1 | 2/2009 | Ibrahim et al. |
| 2009/0062788 A1 | 3/2009 | Long et al. |
| 2009/0076500 A1 | 3/2009 | Azure |
| 2009/0105654 A1 | 4/2009 | Kurth et al. |
| 2009/0149917 A1 | 6/2009 | Whitehurst et al. |
| 2009/0163905 A1 | 6/2009 | Winkler et al. |
| 2009/0228003 A1 | 9/2009 | Sinelnikov |
| 2009/0240248 A1 | 9/2009 | Deford et al. |
| 2009/0275827 A1 | 11/2009 | Aiken et al. |
| 2009/0281477 A1 | 11/2009 | Mikus et al. |
| 2009/0306651 A1 | 12/2009 | Schneider |
| 2010/0004623 A1 | 1/2010 | Hamilton et al. |
| 2010/0023004 A1 | 1/2010 | Francischelli et al. |
| 2010/0137861 A1 | 6/2010 | Soroff et al. |
| 2010/0185140 A1 | 7/2010 | Kassab et al. |
| 2010/0185186 A1 | 7/2010 | Longoria |
| 2010/0191112 A1* | 7/2010 | Demarais ............ A61N 5/0603 601/3 |
| 2010/0191232 A1 | 7/2010 | Boveda |
| 2010/0241185 A1 | 9/2010 | Mahapatra et al. |
| 2010/0261994 A1 | 10/2010 | Davalos et al. |
| 2010/0274238 A1 | 10/2010 | Klimovitch |
| 2010/0280513 A1 | 11/2010 | Juergen et al. |
| 2010/0280539 A1 | 11/2010 | Miyoshi et al. |
| 2010/0292687 A1 | 11/2010 | Kauphusman et al. |
| 2010/0312300 A1 | 12/2010 | Ryu et al. |
| 2011/0028962 A1 | 2/2011 | Werneth et al. |
| 2011/0028964 A1 | 2/2011 | Edwards |
| 2011/0040199 A1 | 2/2011 | Hopenfeld |
| 2011/0098694 A1 | 4/2011 | Long |
| 2011/0106221 A1 | 5/2011 | Neal, II et al. |
| 2011/0130708 A1 | 6/2011 | Perry et al. |
| 2011/0144524 A1 | 6/2011 | Fish et al. |
| 2011/0144633 A1 | 6/2011 | Govari |
| 2011/0160785 A1 | 6/2011 | Mori et al. |
| 2011/0190659 A1 | 8/2011 | Long et al. |
| 2011/0190727 A1 | 8/2011 | Edmunds et al. |
| 2011/0213231 A1 | 9/2011 | Hall et al. |
| 2011/0276047 A1 | 11/2011 | Sklar et al. |
| 2011/0276075 A1 | 11/2011 | Fung et al. |
| 2011/0288544 A1 | 11/2011 | Verin et al. |
| 2011/0313417 A1 | 12/2011 | De La Rama et al. |
| 2012/0029512 A1 | 2/2012 | Willard et al. |
| 2012/0046570 A1 | 2/2012 | Villegas et al. |
| 2012/0053581 A1 | 3/2012 | Wittkampf et al. |
| 2012/0059255 A1 | 3/2012 | Paul et al. |
| 2012/0071872 A1 | 3/2012 | Rubinsky et al. |
| 2012/0089089 A1 | 4/2012 | Swain et al. |
| 2012/0095459 A1 | 4/2012 | Callas et al. |
| 2012/0101413 A1 | 4/2012 | Beetel et al. |
| 2012/0143177 A1* | 6/2012 | Avitall ............... A61B 18/1492 606/41 |
| 2012/0158021 A1 | 6/2012 | Morrill |
| 2012/0165667 A1 | 6/2012 | Altmann et al. |
| 2012/0172859 A1 | 7/2012 | Condie et al. |
| 2012/0172867 A1 | 7/2012 | Ryu et al. |
| 2012/0197100 A1 | 8/2012 | Razavi et al. |
| 2012/0209260 A1 | 8/2012 | Lambert et al. |
| 2012/0220998 A1 | 8/2012 | Long et al. |
| 2012/0232409 A1* | 9/2012 | Stahmann ............ A61B 5/026 600/483 |
| 2012/0265198 A1 | 10/2012 | Crow et al. |
| 2012/0283582 A1 | 11/2012 | Mahapatra et al. |
| 2012/0303019 A1 | 11/2012 | Zhao et al. |
| 2012/0310052 A1 | 12/2012 | Mahapatra et al. |
| 2012/0310230 A1 | 12/2012 | Willis |
| 2012/0310237 A1 | 12/2012 | Swanson |
| 2012/0316557 A1 | 12/2012 | Sartor et al. |
| 2013/0030425 A1* | 1/2013 | Stewart ................ A61B 18/02 606/41 |
| 2013/0030430 A1 | 1/2013 | Stewart et al. |

(56) References Cited

U.S. PATENT DOCUMENTS

| | | |
|---|---|---|
| 2013/0060247 A1 | 3/2013 | Sklar et al. |
| 2013/0060248 A1 | 3/2013 | Sklar et al. |
| 2013/0079768 A1 | 3/2013 | De Luca et al. |
| 2013/0090651 A1 | 4/2013 | Smith |
| 2013/0096655 A1 | 4/2013 | Moffitt et al. |
| 2013/0103027 A1 | 4/2013 | Sklar et al. |
| 2013/0103064 A1 | 4/2013 | Arenson et al. |
| 2013/0131662 A1 | 5/2013 | Wittkampf |
| 2013/0158538 A1 | 6/2013 | Govari |
| 2013/0158621 A1 | 6/2013 | Ding et al. |
| 2013/0165990 A1* | 6/2013 | Mathur .............. A61N 1/06 607/101 |
| 2013/0172715 A1 | 7/2013 | Just et al. |
| 2013/0172864 A1 | 7/2013 | Ibrahim et al. |
| 2013/0172875 A1 | 7/2013 | Govari et al. |
| 2013/0184702 A1 | 7/2013 | Neal, II et al. |
| 2013/0218157 A1 | 8/2013 | Callas et al. |
| 2013/0226174 A1 | 8/2013 | Ibrahim et al. |
| 2013/0237984 A1 | 9/2013 | Sklar |
| 2013/0253415 A1 | 9/2013 | Sano et al. |
| 2013/0296679 A1 | 11/2013 | Condie et al. |
| 2013/0310829 A1 | 11/2013 | Cohen |
| 2013/0317385 A1 | 11/2013 | Sklar et al. |
| 2013/0331831 A1 | 12/2013 | Werneth et al. |
| 2013/0338467 A1 | 12/2013 | Grasse et al. |
| 2013/0345620 A1* | 12/2013 | Zemel ................ A61B 18/042 604/24 |
| 2014/0005664 A1 | 1/2014 | Govari et al. |
| 2014/0024911 A1 | 1/2014 | Harlev et al. |
| 2014/0039288 A1 | 2/2014 | Shih |
| 2014/0051993 A1 | 2/2014 | McGee |
| 2014/0052118 A1 | 2/2014 | Laske et al. |
| 2014/0052126 A1 | 2/2014 | Long et al. |
| 2014/0052216 A1 | 2/2014 | Long et al. |
| 2014/0081113 A1 | 3/2014 | Cohen et al. |
| 2014/0100563 A1 | 4/2014 | Govari et al. |
| 2014/0107644 A1 | 4/2014 | Falwell et al. |
| 2014/0142408 A1 | 5/2014 | De La Rama et al. |
| 2014/0148804 A1 | 5/2014 | Ward et al. |
| 2014/0163480 A1 | 6/2014 | Govari et al. |
| 2014/0163546 A1 | 6/2014 | Govari et al. |
| 2014/0171942 A1 | 6/2014 | Werneth et al. |
| 2014/0180035 A1 | 6/2014 | Anderson |
| 2014/0194716 A1 | 7/2014 | Diep et al. |
| 2014/0194867 A1 | 7/2014 | Fish et al. |
| 2014/0200567 A1 | 7/2014 | Cox et al. |
| 2014/0235986 A1 | 8/2014 | Harlev et al. |
| 2014/0235988 A1 | 8/2014 | Ghosh |
| 2014/0235989 A1 | 8/2014 | Wodlinger et al. |
| 2014/0243851 A1 | 8/2014 | Cohen et al. |
| 2014/0276760 A1 | 9/2014 | Bonyak et al. |
| 2014/0276782 A1 | 9/2014 | Paskar |
| 2014/0276791 A1 | 9/2014 | Ku et al. |
| 2014/0288556 A1 | 9/2014 | Ibrahim et al. |
| 2014/0303721 A1 | 10/2014 | Fung et al. |
| 2014/0343549 A1 | 11/2014 | Spear et al. |
| 2014/0364845 A1 | 12/2014 | Rashidi |
| 2014/0371613 A1 | 12/2014 | Narayan et al. |
| 2015/0005767 A1 | 1/2015 | Werneth et al. |
| 2015/0011995 A1 | 1/2015 | Avitall et al. |
| 2015/0066108 A1 | 3/2015 | Shi et al. |
| 2015/0126840 A1 | 5/2015 | Thakur et al. |
| 2015/0133914 A1 | 5/2015 | Koblish |
| 2015/0138977 A1 | 5/2015 | Dacosta |
| 2015/0141978 A1 | 5/2015 | Subramaniam et al. |
| 2015/0142041 A1 | 5/2015 | Kendale et al. |
| 2015/0148796 A1 | 5/2015 | Bencini |
| 2015/0150472 A1 | 6/2015 | Harlev et al. |
| 2015/0157402 A1 | 6/2015 | Kunis et al. |
| 2015/0157412 A1 | 6/2015 | Wallace et al. |
| 2015/0164584 A1 | 6/2015 | Davalos et al. |
| 2015/0173824 A1 | 6/2015 | Davalos et al. |
| 2015/0173828 A1 | 6/2015 | Avitall |
| 2015/0174404 A1 | 6/2015 | Rousso et al. |
| 2015/0182740 A1 | 7/2015 | Mickelsen |
| 2015/0196217 A1 | 7/2015 | Harlev et al. |
| 2015/0223726 A1 | 8/2015 | Harlev et al. |
| 2015/0230699 A1 | 8/2015 | Berul et al. |
| 2015/0258344 A1 | 9/2015 | Tandri et al. |
| 2015/0265342 A1 | 9/2015 | Long et al. |
| 2015/0265344 A1 | 9/2015 | Aktas et al. |
| 2015/0272656 A1 | 10/2015 | Chen |
| 2015/0272664 A9 | 10/2015 | Cohen |
| 2015/0272667 A1 | 10/2015 | Govari et al. |
| 2015/0282729 A1 | 10/2015 | Harlev et al. |
| 2015/0289923 A1 | 10/2015 | Davalos et al. |
| 2015/0304879 A1 | 10/2015 | Dacosta |
| 2015/0320481 A1 | 11/2015 | Cosman et al. |
| 2015/0321021 A1 | 11/2015 | Tandri et al. |
| 2015/0342532 A1 | 12/2015 | Basu et al. |
| 2015/0343212 A1 | 12/2015 | Rousso et al. |
| 2015/0351836 A1 | 12/2015 | Prutchi |
| 2015/0359583 A1 | 12/2015 | Swanson |
| 2016/0000500 A1 | 1/2016 | Salahieh et al. |
| 2016/0008061 A1 | 1/2016 | Fung et al. |
| 2016/0008065 A1 | 1/2016 | Gliner et al. |
| 2016/0029960 A1 | 2/2016 | Toth et al. |
| 2016/0038772 A1 | 2/2016 | Thapliyal et al. |
| 2016/0051204 A1 | 2/2016 | Harlev et al. |
| 2016/0051324 A1 | 2/2016 | Stewart et al. |
| 2016/0058493 A1 | 3/2016 | Neal, II et al. |
| 2016/0058506 A1 | 3/2016 | Spence et al. |
| 2016/0066993 A1 | 3/2016 | Avitall et al. |
| 2016/0074679 A1 | 3/2016 | Thapliyal et al. |
| 2016/0095531 A1 | 4/2016 | Narayan et al. |
| 2016/0095642 A1 | 4/2016 | Deno et al. |
| 2016/0095653 A1 | 4/2016 | Lambert et al. |
| 2016/0100797 A1 | 4/2016 | Mahapatra et al. |
| 2016/0100884 A1 | 4/2016 | Fay et al. |
| 2016/0106498 A1 | 4/2016 | Highsmith et al. |
| 2016/0106500 A1 | 4/2016 | Olson |
| 2016/0113709 A1 | 4/2016 | Maor |
| 2016/0113712 A1 | 4/2016 | Cheung et al. |
| 2016/0120564 A1 | 5/2016 | Kirkpatrick et al. |
| 2016/0128770 A1 | 5/2016 | Afonso et al. |
| 2016/0166167 A1 | 6/2016 | Narayan et al. |
| 2016/0166310 A1 | 6/2016 | Stewart et al. |
| 2016/0166311 A1 | 6/2016 | Long et al. |
| 2016/0174865 A1 | 6/2016 | Stewart et al. |
| 2016/0183877 A1 | 6/2016 | Williams et al. |
| 2016/0184003 A1 | 6/2016 | Srimathveeravalli et al. |
| 2016/0213282 A1 | 7/2016 | Leo et al. |
| 2016/0220307 A1 | 8/2016 | Miller et al. |
| 2016/0235470 A1 | 8/2016 | Callas et al. |
| 2016/0287314 A1 | 10/2016 | Arena et al. |
| 2016/0310211 A1 | 10/2016 | Long |
| 2016/0324564 A1 | 11/2016 | Gerlach et al. |
| 2016/0324573 A1 | 11/2016 | Mickelsen et al. |
| 2016/0331441 A1 | 11/2016 | Konings |
| 2016/0331459 A1 | 11/2016 | Townley et al. |
| 2016/0354142 A1 | 12/2016 | Pearson et al. |
| 2016/0361109 A1 | 12/2016 | Weaver et al. |
| 2017/0035499 A1 | 2/2017 | Stewart et al. |
| 2017/0042449 A1 | 2/2017 | Deno et al. |
| 2017/0042615 A1 | 2/2017 | Salahieh et al. |
| 2017/0056648 A1 | 3/2017 | Syed et al. |
| 2017/0065330 A1 | 3/2017 | Mickelsen et al. |
| 2017/0065339 A1 | 3/2017 | Mickelsen |
| 2017/0065340 A1 | 3/2017 | Long |
| 2017/0065343 A1 | 3/2017 | Mickelsen |
| 2017/0071543 A1 | 3/2017 | Basu et al. |
| 2017/0095291 A1 | 4/2017 | Harrington et al. |
| 2017/0105793 A1 | 4/2017 | Cao et al. |
| 2017/0151029 A1 | 6/2017 | Mickelsen |
| 2017/0172654 A1 | 6/2017 | Wittkampf et al. |
| 2017/0181795 A1 | 6/2017 | Debruyne |
| 2017/0189097 A1 | 7/2017 | Viswanathan et al. |
| 2017/0215953 A1 | 8/2017 | Long et al. |
| 2017/0245928 A1 | 8/2017 | Xiao et al. |
| 2017/0246455 A1 | 8/2017 | Athos et al. |
| 2017/0312024 A1 | 11/2017 | Harlev et al. |
| 2017/0312025 A1 | 11/2017 | Harlev et al. |
| 2017/0312027 A1 | 11/2017 | Harlev et al. |
| 2018/0001056 A1 | 1/2018 | Leeflang et al. |

(56) References Cited

U.S. PATENT DOCUMENTS

| | | |
|---|---|---|
| 2018/0042674 A1 | 2/2018 | Mickelsen |
| 2018/0042675 A1 | 2/2018 | Long |
| 2018/0043153 A1 | 2/2018 | Viswanathan et al. |
| 2018/0064488 A1 | 3/2018 | Long et al. |
| 2018/0085160 A1 | 3/2018 | Viswanathan et al. |
| 2018/0093088 A1 | 4/2018 | Mickelsen |
| 2018/0133460 A1 | 5/2018 | Townley et al. |
| 2018/0184982 A1 | 7/2018 | Basu et al. |
| 2018/0193090 A1 | 7/2018 | de la Rama et al. |
| 2018/0200497 A1 | 7/2018 | Mickelsen |
| 2018/0303488 A1 | 10/2018 | Hill |
| 2018/0311497 A1 | 11/2018 | Viswanathan et al. |
| 2018/0344393 A1 | 12/2018 | Gruba et al. |
| 2018/0360534 A1 | 12/2018 | Teplitsky et al. |
| 2019/0069950 A1 | 3/2019 | Viswanathan et al. |
| 2019/0183378 A1 | 6/2019 | Mosesov et al. |
| 2019/0201089 A1 | 7/2019 | Waldstreicher et al. |
| 2019/0231425 A1 | 8/2019 | Waldstreicher et al. |
| 2019/0336198 A1 | 11/2019 | Viswanathan et al. |
| 2019/0336207 A1 | 11/2019 | Viswanathan |
| 2021/0015550 A1 | 1/2021 | Highsmith et al. |

FOREIGN PATENT DOCUMENTS

| | | |
|---|---|---|
| EP | 1127552 | 6/2006 |
| EP | 1340469 | 3/2007 |
| EP | 1009303 | 6/2009 |
| EP | 2213729 | 8/2010 |
| EP | 2425871 | 3/2012 |
| EP | 1803411 | 8/2012 |
| EP | 2532320 A2 | 12/2012 |
| EP | 2587275 | 5/2013 |
| EP | 2663227 | 11/2013 |
| EP | 1909678 | 1/2014 |
| EP | 2217165 | 3/2014 |
| EP | 2376193 | 3/2014 |
| EP | 2708181 | 3/2014 |
| EP | 2777579 A1 | 9/2014 |
| EP | 2934307 | 10/2015 |
| EP | 2777585 | 6/2016 |
| EP | 2382935 B1 | 3/2018 |
| EP | 3111871 B1 | 3/2018 |
| EP | 3151773 B1 | 4/2018 |
| EP | 3056242 B1 | 7/2018 |
| JP | H06-507797 | 9/1994 |
| JP | 2000-508196 | 7/2000 |
| JP | 2005-516666 | 6/2005 |
| JP | 2006-506184 | 2/2006 |
| JP | 2008-538997 | 11/2008 |
| JP | 2009-500129 | 1/2009 |
| JP | 2011-509158 | 3/2011 |
| JP | 2012-050538 | 3/2012 |
| WO | WO 92/07622 | 5/1992 |
| WO | WO 92/21278 | 12/1992 |
| WO | WO 92/21285 | 12/1992 |
| WO | WO 97/24073 | 7/1997 |
| WO | WO 97/25917 | 7/1997 |
| WO | WO 97/37719 | 10/1997 |
| WO | WO 1999/004851 | 2/1999 |
| WO | WO 1999/022659 | 5/1999 |
| WO | WO 2002/056782 | 7/2002 |
| WO | WO 2003/065916 | 8/2003 |
| WO | WO 2004/045442 | 6/2004 |
| WO | WO 2004/086994 | 10/2004 |
| WO | WO 2005/046487 | 5/2005 |
| WO | WO 2006/115902 | 11/2006 |
| WO | WO 2007/006055 | 1/2007 |
| WO | WO 2007/079438 | 7/2007 |
| WO | WO 2009/082710 | 7/2009 |
| WO | WO 2009/089343 | 7/2009 |
| WO | WO 2009/137800 | 11/2009 |
| WO | WO 2010/014480 | 2/2010 |
| WO | WO 2011/028310 | 3/2011 |
| WO | WO 2011/154805 | 12/2011 |
| WO | WO 2012/051433 | 4/2012 |
| WO | WO 2012/153928 | 11/2012 |
| WO | WO 2013/019385 | 2/2013 |
| WO | WO 2014/025394 | 2/2014 |
| WO | WO 2014/031800 | 2/2014 |
| WO | WO 2014/036439 | 3/2014 |
| WO | WO 2014/160832 | 10/2014 |
| WO | WO 2015/066322 | 5/2015 |
| WO | WO 2015/099786 | 7/2015 |
| WO | WO 2015/103530 | 7/2015 |
| WO | WO 2015/103574 | 7/2015 |
| WO | WO 2015/130824 | 9/2015 |
| WO | WO 2015/140741 | 9/2015 |
| WO | WO 2015/143327 | 9/2015 |
| WO | WO 2015/171921 | 11/2015 |
| WO | WO 2015/175944 | 11/2015 |
| WO | WO 2015/192018 | 12/2015 |
| WO | WO 2015/192027 | 12/2015 |
| WO | WO 2016/059027 | 4/2016 |
| WO | WO 2016/060983 | 4/2016 |
| WO | WO 2016/081650 | 5/2016 |
| WO | WO 2016/090175 | 6/2016 |
| WO | WO 2017/093926 | 6/2017 |
| WO | WO 2017/119934 | 7/2017 |
| WO | WO 2017/120169 | 7/2017 |
| WO | WO 2017/192477 | 11/2017 |
| WO | WO 2017/192495 | 11/2017 |
| WO | WO 2017/218734 | 12/2017 |
| WO | WO 2018/005511 | 1/2018 |
| WO | WO 2018/200800 | 11/2018 |
| WO | WO 2019/133606 | 7/2019 |
| WO | WO 2020/236558 | 11/2020 |

OTHER PUBLICATIONS

Partial Supplementary European Search Report for European Application No. 13827672.0, dated Mar. 23, 2016, 6 pages.
Supplementary European Search Report for European Application No. 13827672.0, dated Jul. 11, 2016, 12 pages.
Office Action for European Application No. 13827672.0, dated Feb. 5, 2018, 6 pages.
Notice of Reasons for Rejection for Japanese Application No. 2015-526522, dated Mar. 6, 2017, 3 pages.
Office Action for U.S. Appl. No. 14/400,455, dated Mar. 30, 2017, 10 pages.
International Search Report and Written Opinion for International Application No. PCT/US2013/031252, dated Jul. 19, 2013, 12 pages.
Office Action for Japanese Application No. 2018-036714, dated Jan. 16, 2019, 8 pages.
Office Action for U.S. Appl. No. 15/819,726, dated Jun. 4, 2018, 17 pages.
Office Action for U.S. Appl. No. 15/917,194, dated Jun. 4, 2018, 17 pages.
Office Action for U.S. Appl. No. 15/917,194, dated Oct. 9, 2018, 13 pages.
Office Action for U.S. Appl. No. 15/917,194, dated Apr. 29, 2019, 10 pages.
First Office Action for Chinese Application No. 201580006848.8, dated Jan. 29, 2018, 15 pages.
Office Action for European Application No. 15701856.5, dated Dec. 11, 2017, 6 pages.
Notice of Reasons for Rejection for Japanese Application No. 2016-544072, dated Oct. 1, 2018, 11 pages.
Office Action for U.S. Appl. No. 15/201,983, dated Apr. 3, 2019, 16 pages.
International Search Report and Written Opinion for International Application No. PCT/US2015/010138, dated Mar. 26, 2015, 14 pages.
International Preliminary Report on Patentability for International Application No. PCT/US2015/010138, dated Jul. 12, 2016, 9 pages.
Supplementary European Search Report for European Application No. 15733297.4, dated Aug. 10, 2017, 7 pages.
Office Action for U.S. Appl. No. 15/201,997, dated Apr. 3, 2017, 6 pages.

(56) References Cited

OTHER PUBLICATIONS

Office Action for U.S. Appl. No. 15/201,997, dated Aug. 29, 2017, 12 pages.
Office Action for U.S. Appl. No. 15/201,997, dated Jul. 12, 2018, 12 pages.
Office Action for U.S. Appl. No. 15/201,997, dated Dec. 17, 2018, 17 pages.
International Search Report and Written Opinion for International Application No. PCT/US2015/010223, dated Apr. 10, 2015, 19 pages.
International Preliminary Report on Patentability for International Application No. PCT/US2015/010223, dated Jul. 12, 2016, 12 pages.
International Search Report and Written Opinion for International Application No. PCT/US2015/029734, dated Nov. 24, 2015, 15 pages.
Extended European Search Report for European Application No. 18189811.5, dated May 14, 2019, 7 pages.
Office Action for U.S. Appl. No. 15/795,062, dated Dec. 19, 2017, 14 pages.
Office Action for U.S. Appl. No. 15/795,062, dated Apr. 9, 2018, 20 pages.
Office Action for U.S. Appl. No. 15/795,062, dated May 3, 2019, 21 pages.
Office Action for U.S. Appl. No. 15/341,523, dated Jan. 29, 2019, 10 pages.
International Search Report and Written Opinion for International Application No. PCT/US2015/031086, dated Oct. 21, 2015, 16 pages.
Office Action for U.S. Appl. No. 15/795,075, dated Feb. 6, 2018, 9 pages.
Office Action for U.S. Appl. No. 15/795,075, dated Jun. 15, 2018, 10 pages.
Office Action for U.S. Appl. No. 15/795,075, dated Apr. 10, 2019, 11 pages.
Extended European Search Report for European Application No. 15849844.4, dated May 3, 2018, 8 pages.
International Search Report and Written Opinion for International Application No. PCT/US2015/055105, dated Mar. 1, 2016, 15 pages.
Office Action for U.S. Appl. No. 15/796,255, dated Jan. 10, 2018, 12 pages.
Extended European Search Report for European Application No. 15806855.1, dated Jan. 3, 2018, 8 pages.
International Search Report and Written Opinion for International Application No. PCT/US2015/035582, dated Oct. 2, 2015, 17 pages.
Extended European Search Report for European Application No. 15806278.6, dated Feb. 9, 2018, 5 pages.
International Search Report and Written Opinion for International Application No. PCT/US2015/035592, dated Oct. 2, 2015, 13 pages.
Office Action for U.S. Appl. No. 15/334,646, dated Jul. 25, 2017, 19 pages.
Office Action for U.S. Appl. No. 15/334,646, dated Nov. 16, 2017, 26 pages.
International Search Report and Written Opinion for International Application No. PCT/US2016/057664, dated Feb. 24, 2017, 11 pages.
Office Action for U.S. Appl. No. 15/796,375, dated Jan. 24, 2018, 25 pages.
Office Action for U.S. Appl. No. 15/796,375, dated May 30, 2018, 26 pages.
Office Action for U.S. Appl. No. 15/796,375, dated Nov. 16, 2018, 27 pages.
International Search Report and Written Opinion for International Application No. PCT/US2017/012099, dated May 18, 2017, 17 pages.

Office Action for U.S. Appl. No. 15/711,266, dated Feb. 23, 2018, 14 pages.
International Search Report and Written Opinion for International Application No. PCT/US2018/029938, dated Aug. 29, 2018, 14 pages.
International Search Report and Written Opinion for International Application No. PCT/US2019/014226, dated Apr. 29, 2019, 15 pages.
International Search Report and Written Opinion for International Application No. PCT/US2017/037609, dated Nov. 8, 2017, 13 pages.
Office Action for U.S. Appl. No. 15/672,916, dated Feb. 13, 2018, 16 pages.
Office Action for U.S. Appl. No. 15/672,916, dated Jul. 20, 2018, 23 pages.
Office Action for U.S. Appl. No. 15/672,916, dated Apr. 9, 2019, 31 pages.
Office Action for U.S. Appl. No. 15/499,804, dated Jan. 3, 2018, 20 pages.
Office Action for U.S. Appl. No. 15/794,717, dated Feb. 1, 2018, 10 pages.
International Search Report and Written Opinion for International Application No. PCT/US2018/029552, dated Jun. 29, 2018, 13 pages.
Partial European Search Report for European Application No. 18170210.1, dated Feb. 14, 2019, 13 pages.
International Search Report and Written Opinion for International Application No. PCT/US2018/050660, dated Nov. 26, 2018, 13 pages.
Office Action for U.S. Appl. No. 15/970,404, dated Oct. 9, 2018, 21 pages.
Office Action for U.S. Appl. No. 15/970,404, dated Apr. 12, 2019, 20 pages.
International Search Report and Written Opinion for International Application No. PCT/US2019/017322, dated May 10, 2019, 15 pages.
Du Pre, B.C. et al., "Minimal coronary artery damage by myocardial electroporation ablation," Europace, 15(1):144-149 (2013).
Hobbs, E. P., "Investor Relations Update: Tissue Ablation via Irreversible Electroporation (IRE)," Powerpoint (2004), 16 pages.
Lavee, J. et al., "A Novel Nonthermal Energy Source for Surgical Epicardial Atrial Ablation: Irreversible Electroporation," The Heart Surgery Forum #2006-1202, 10(2), 2007 [Epub Mar. 2007].
Madhavan, M. et al., "Novel Percutaneous Epicardial Autonomic Modulation in the Canine for Atrial Fibrillation: Results of an Efficacy and Safety Study," Pace, 00:1-11 (2016).
Neven, K. et al., "Safety and Feasibility of Closed Chest Epicardial Catheter Ablation Using Electroporation," Circ Arrhythm Electrophysiol., 7:913-919 (2014).
Neven, K. et al., "Myocardial Lesion Size After Epicardial Electroporation Catheter Ablation After Subxiphoid Puncture," Circ Arrhythm Electrophysiol., 7(4):728-733 (2014).
Neven, K. et al., "Epicardial linear electroporation ablation and lesion size," Heart Rhythm, 11:1465-1470 (2014).
Van Driel, V.J.H.M. et al., "Pulmonary Vein Stenosis After Catheter Ablation Electroporation Versus Radiofrequency," Circ Arrhythm Electrophysiol., 7(4):734-738 (2014).
Van Driel, V.J.H.M. et al., "Low vulnerability of the right phrenic nerve to electroporation ablation," Heart Rhythm, 12:1838-1844 (2015).
Wittkampf, F.H. et al., "Myocardial Lesion Depth With Circular Electroporation Ablation," Circ. Arrhythm Electrophysiol., 5(3):581-586 (2012).
Wittkampf, F.H. et al., "Feasibility of Electroporation for the Creation of Pulmonary Vein Ostial Lesions," J Cardiovasc Electrophysiol, 22(3):302-309 (Mar. 2011).

* cited by examiner

APPARATUS AND METHODS FOR RENAL DENERVATION ABLATION

CROSS-REFERENCE TO RELATED APPLICATIONS

This application is a division of U.S. patent application Ser. No. 15/201,997 filed Jul. 5, 2016, entitled "APPARATUS AND METHODS FOR RENAL DENERVATION ABLATION," now issued as U.S. Pat. No. 10,517,672, which is a continuation of PCT/US2015/010223 filed Jan. 6, 2015, entitled "APPARATUS AND METHODS FOR RENAL DENERVATION ABLATION," which claims priority to and the benefit of U.S. Provisional Application No. 61/923,969 filed Jan. 6, 2014, entitled "BALLOON CATHETER WITH BLOOD PATH," and U.S. Provisional Application No. 61/923,966 filed Jan. 6, 2014, entitled "OFFSET RENAL DENERVATION ELECTRODE," each of which are incorporated by reference herein in their entirety.

BACKGROUND

This application is in the general field of therapeutic electrical energy delivery, and it pertains more specifically to electrical energy delivery in the context of ablation of nerves in the vascular or vessel walls of renal arteries or renal denervation, a therapeutic procedure that can lead to reduced hypertension in patients with high blood pressure. The ablation energy can be in the form of high voltage DC pulses that generate irreversible electroporation of cell membranes and destroy tissue locally for therapeutic purposes, or it can be applied as RF energy that generates thermal energy.

The past two decades have seen advances in the technique of electroporation as it has progressed from the laboratory to clinical applications. Known methods include applying brief, high voltage DC pulses to tissue, thereby generating locally high electric fields, typically in the range of hundreds of Volts/centimeter. The electric fields disrupt cell membranes by generating pores in the cell membrane, which subsequently destroys the cell membrane and the cell. While the precise mechanism of this electrically-driven pore generation (or electroporation) awaits a detailed understanding, it is thought that the application of relatively large electric fields generates instabilities in the phospholipid bilayers in cell membranes, as well as mitochondria, causing the occurrence of a distribution of local gaps or pores in the membrane. If the applied electric field at the membrane exceeds a threshold value, typically dependent on cell size, the electroporation is irreversible and the pores remain open, permitting exchange of material across the membrane and leading to apoptosis or cell death. Subsequently, the surrounding tissue heals in a natural process.

While pulsed DC voltages are known to drive electroporation under the right circumstances, the examples of irreversible electroporation applications in medicine and delivery methods described in the prior art do not provide specific means of limiting possible damage to nearby tissue while it is desired to ablate tissue relatively farther away. There is a need for selective energy delivery methods and devices that generate tissue ablation where it is desired, while leaving tissue elsewhere relatively intact and unchanged. In the specific context of minimally invasive renal denervation for the treatment of hypertension, known ablation devices are generally positioned in the renal arteries for electrical energy delivery to the renal artery walls. The outer layers of the renal arteries, or adventitia, have a distribution of renal nerve endings. When these nerve endings are destroyed by application of a high electric field, the consequent reduction in renal sympathetic activity can result in decreased hypertension. During this process, the vessel wall must be maintained intact; the local electric field in the vessel wall must not be too large, in order to avoid generating locally large current densities in the vessel wall which can lead to local thermal "hot spots" that can unintentionally damage or perforate the renal vessel. Thus it is desired to maintain vessel integrity and reduce and/or avoid local thermal hot spots driven by locally large current densities while still maintaining an electric field magnitude that is still above the threshold of irreversible electroporation.

There is a need for selective energy delivery for electroporation in such a manner as to preserve overall vascular integrity while destroying the nerve endings in the adventitia of the renal artery where ablation is to be performed.

SUMMARY

The present disclosure addresses the need for tools and methods for rapid and selective application of electroporation therapy in the treatment of hypertension by minimally invasive ablation of the renal arteries. The embodiments described herein can result in well-controlled and specific delivery of electroporation in an efficacious manner while preserving vascular tissue where the local damage is to be preferentially minimized by reducing and/or eliminating thermal hot spots (or localized areas of high temperature and/or spatial temperature gradients), in order to maintain overall vascular integrity. In some embodiments, an apparatus includes a flexible catheter shaft and at least one electrode pair. The flexible catheter shaft has an electrically insulating expandable member coupled thereto such that the expandable member surrounds a portion of the catheter shaft. The portion of the catheter shaft defines a lumen, and a surface of the catheter shaft defines a first opening and a second opening. The first opening and the second opening are each in fluid communication with the lumen. The expandable member is disposed between the first opening and the second opening to establish a pathway through the expandable member via the lumen. The electrode pair includes a first electrode and a second electrode. The first electrode is coupled to the catheter shaft between the first opening and the expandable member. The second electrode is coupled to the catheter shaft between the second opening and the expandable member.

In some embodiments, a method includes using the catheter device and systems for the selective and rapid application of DC voltage to produce electroporation ablation for renal denervation. For example, in some embodiments, an irreversible electroporation system includes a DC voltage/signal generator and a controller for triggering voltage pulses to be applied to a selected multiplicity or a subset of electrodes. The catheter device has a set of electrodes for ablation or delivery of voltage pulses, and an expandable member (e.g., an inflatable balloon) disposed between a pair of electrodes. When the expandable member is moved to an expanded configuration (e.g., the balloon is inflated), the electrodes are positioned in the central region of the vessel lumen, away from the vessel wall. Furthermore, the catheter has openings from the exterior surface into an internal lumen that runs along a path approximately parallel to the longitudinal axis of the balloon, and with a lumen length that extends beyond either electrode of the electrode pair. Thus, the internal lumen provides an internal path in the device for blood flow through the renal vessel. When the balloon is inflated and blocks most of the vessel lumen, blood can still flow from one end of the balloon to the other through the internal blood path in the catheter. Thus, vessel occlusion of blood flow does not occur. The internal blood path also provides a shunt path for electric current to flow through when the electrodes on either end of the balloon are polarized. This shunt path for electric current also serves to reduce electric field intensities in corner regions between the balloon and the vessel wall, suppressing or eliminating local or regional hot spots where large current density values can drive local thermal heating of vascular tissue, resulting in a safer and more effective ablation device. Thus, the intense electric field near or in the internal vessel wall is reduced and/or eliminated, reducing the likelihood of vessel wall perforation. The electric field magnitude in the vessel wall can remain large enough to generate irreversible electroporation of the renal nerve endings therein.

In some embodiments, the catheter device has a set of electrodes for ablation or delivery of voltage pulses, at least one member of which is recessed from the outer surface such that when inserted in a vascular structure, it cannot directly contact the inner vascular wall. The recessed electrode contacts blood in the vessel, with blood forming a portion of the electrical path between anode and cathode electrodes, and with the vascular wall also forming a portion of the electrical path between anode and cathode electrodes. In some embodiments, all of the electrodes on the catheter are recessed so that there is no direct physical contact between any of the electrodes and the vascular wall. Thus, the intense electric field near the electrode surface is removed from the wall, reducing or eliminating the likelihood of vessel wall perforation. The electric field magnitude in the vessel wall, however, is large enough to generate irreversible electroporation of the renal nerve endings therein. In some embodiments, at least one pair of anode and cathode electrodes are set in a recessed void in the catheter, and separated from each other by an insulator. In general, the catheter can have a multiplicity of such pairs of anode and cathode electrodes recessed in the catheter, so as to be able to ablate a longer region or length of arterial wall more conveniently.

In some embodiments, for example, the voltage pulses can have pulse widths in the range of nanoseconds to hundreds of microseconds. In some embodiments, there could be a multiplicity of such voltage pulses applied through the electrodes, with an interval between pulses that can for illustrative purposes be in the range of nanoseconds to hundreds of microseconds. The generator can output waveforms that can be selected to generate a sequence of voltage pulses in either monophasic or multiphasic forms and with either constant or progressively changing amplitudes.

DETAILED DESCRIPTION

Figure 1:
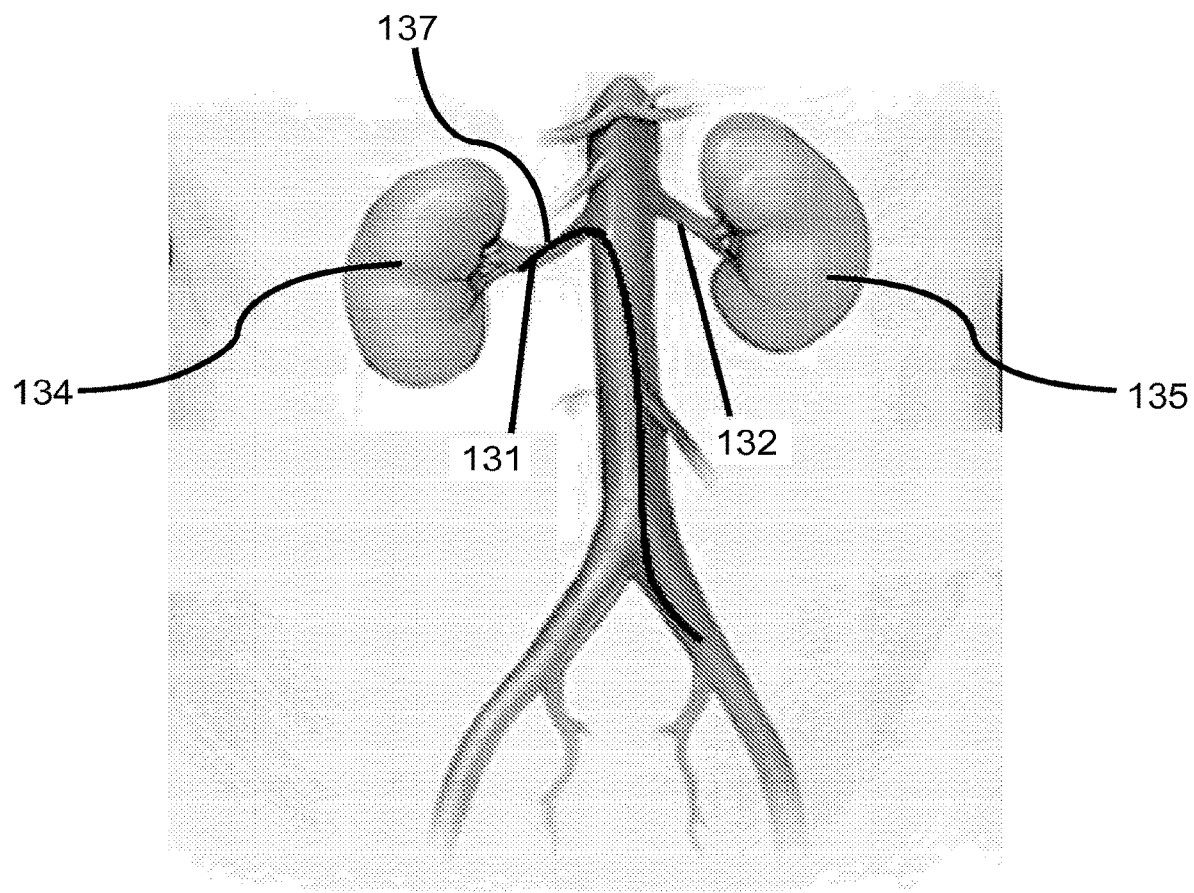
FIG. 1 illustrates the placement of a catheter device according to an embodiment in the renal arteries for the purpose of renal denervation.

This embodiments described herein include a catheter device and systems for renal denervation ablation with rapid application of DC high voltage pulses to drive irreversible electroporation. In some embodiments, the irreversible electroporation system described herein includes a DC voltage pulse/signal generator and a controller capable of being configured to apply voltages to a selected multiplicity of electrodes.

In some embodiments, the catheter has an inflatable balloon or similar expandable member disposed in its distal portion such that the catheter shaft passes through the balloon. The catheter has at least one anode-cathode pair of electrodes that are disposed on either end of the expandable member or inflatable balloon in the distal region of the catheter. With the balloon inflated, the electrodes are positioned in the central region of the vessel lumen and away from the vessel wall. Furthermore, the catheter has openings from the exterior surface into an internal lumen that runs along a path approximately parallel to the longitudinal axis of the catheter/balloon, and with a lumen length that extends beyond either electrode of the electrode pair. Thus, the internal lumen provides an internal path for blood flow in the device starting from a location proximal to the proximal electrode and ending at a location distal to the distal electrode, thus shunting blood flowing through the renal vessel. In this manner, when the balloon is inflated and blocks most of the vessel lumen, blood can still flow from one end of the balloon to the other through the internal blood path in the catheter. Thus, vessel occlusion of blood flow does not occur.

Moreover, in some embodiments, the internal blood path also provides a shunt path for electric current to flow through when the electrodes on either end of the balloon are polarized by an applied potential difference. This shunt path for electric current also serves to reduce electric field intensities in corner regions between the balloon and the vessel wall, suppressing or eliminating local or regional hot spots where large current density values can drive local thermal heating of vascular tissue, thereby resulting in an overall safer and more effective ablation device. Thus, the intense electric field and associated large current density near or in the internal vascular wall is eliminated, reducing the likelihood of vessel wall perforation.

The electric field magnitude in the vessel wall, however, can remain large enough to generate irreversible electroporation of the renal nerve endings therein and successful ablation results. In some embodiments, the voltage pulses can have pulse widths in the range of nanoseconds to hundreds of microseconds. In some embodiments, there could be a multiplicity of such voltage pulses applied through the electrodes, with an interval between pulses that can for illustrative purposes be in the range of nanoseconds to hundreds of microseconds. The generator can output waveforms that can be selected to generate a sequence of voltage pulses in either monophasic or multiphasic forms and with either constant or progressively changing amplitudes.

The balloons and/or expandable members described herein can be constructed from any suitable material. For example, in some embodiments, the balloon is made of a material that is electrically an insulator such as for example polyurethane.

In some embodiments, an apparatus includes a flexible catheter shaft and at least one electrode pair. The flexible catheter shaft has an electrically insulating expandable member coupled thereto such that the expandable member surrounds a portion of the catheter shaft. The portion of the catheter shaft defines a lumen, and a surface of the catheter shaft defines a first opening and a second opening. The first opening and the second opening are each in fluid communication with the lumen. The expandable member is disposed between the first opening and the second opening to establish a pathway through the expandable member via the lumen. The electrode pair includes a first electrode and a second electrode. The first electrode is coupled to the catheter shaft between the first opening and the expandable member. The second electrode is coupled to the catheter shaft between the second opening and the expandable member.

In some embodiments, a method includes inserting a catheter device comprising a flexible catheter shaft and at least one electrode pair into a renal artery. The flexible catheter shaft has an electrically insulating expandable member coupled thereto such that the expandable member surrounds a portion of the catheter shaft. The expandable member is expanded until in expanded form it abuts the arterial vessel wall around its circumference, thereby positioning the catheter device so that it becomes well-centered within the vessel lumen. The portion of the catheter shaft surrounded by the expandable member defines a lumen, and a surface of the catheter shaft defines a first opening and a second opening each in fluid communication with the lumen. With the expandable member in expanded form, the first and second openings in the catheter shaft surface and the lumen together provide a path for blood flow to continue in the arterial vessel, even when the expanded member occludes longitudinal blood flow in the circumferential portions of the vessel cross section. With the device thus deployed, a voltage pulse for tissue ablation is applied between the electrodes of the electrode pair, ablating the nerve endings in the renal arterial wall. Subsequently, the expandable member is relaxed or returned to unexpanded form, and the catheter device is inserted further into the renal arterial vessel for ablation at a subsequent location, and so on. The iterative steps of inserting and positioning the catheter device and applying ablation are continued as needed until the user decides that a sufficient degree of ablation has been applied.

An anatomical pathway and context for use of the catheter device according to an embodiment in a renal denervation ablation procedure is illustrated in FIG. 1, illustrating the placement of a catheter device in the renal arteries for this purpose. FIG. 1 depicts a left (patient left) kidney 135 and a right kidney 134 together with left renal artery 132 and right renal artery 131. Any of the catheter devices shown and described herein can be inserted into the vascular anatomy via, for example, femoral access and the distal portion 137 of the catheter is shown disposed within right renal artery 131. Ablation pulses are applied at such a location or at a multiplicity of similar locations in the renal artery to destroy renal nerve endings in the vessel wall of the renal artery.

Figure 2:
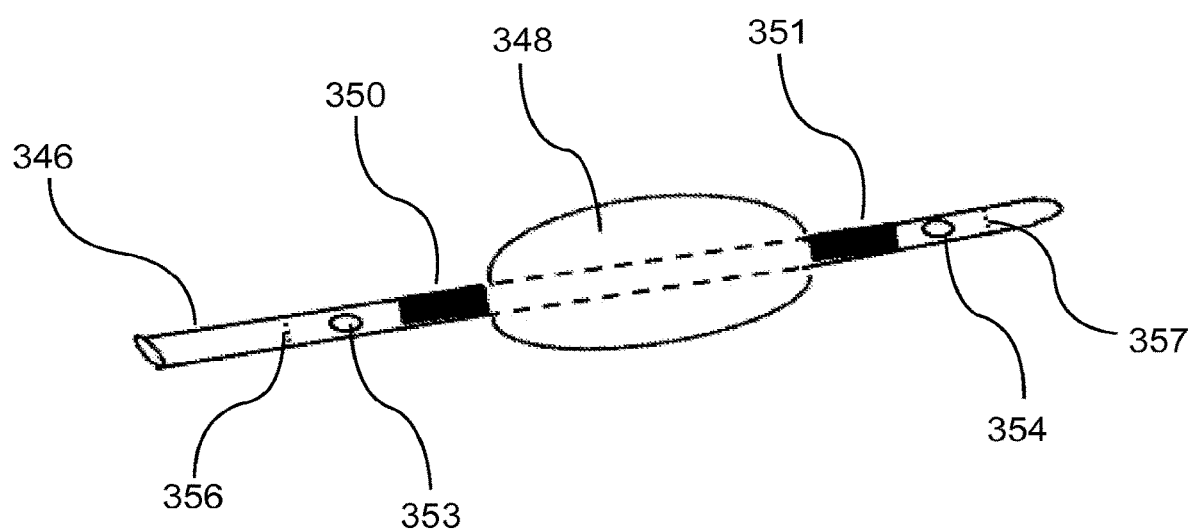
FIG. 2 is a schematic illustration of a catheter assembly according to an embodiment showing an expandable member on a catheter shaft with electrodes disposed on the shaft near the ends of the expandable member, and showing openings in the catheter shaft into an internal device lumen that provides a blood path for blood flow.

A catheter assembly according to an embodiment is illustrated in FIG. 2 in schematic form showing an expanded member (for purposes of non-limiting example, one form of the expanded member can be an inflated catheter balloon) on a catheter shaft with electrodes disposed on the shaft near the ends of the balloon. As shown in FIG. 2, the distal portion of the catheter 346 has an inflatable balloon 348 disposed between proximal electrode 350 and distal electrode 351 located on either side (forward or backward along the device longitudinal axis) of the balloon. The electrodes are disposed with conducting surfaces exposed to the blood flow. Thus, the electrodes could be, for example, in the form of ring electrodes mounted on the catheter shaft and attached by an etching and gluing process, or swaged or crimped in place, or otherwise mounted by any of a range of processes known to those skilled in the art. Furthermore, an internal lumen for blood flow is present in the device between internal lumen end sections 356 and 357. The catheter shaft has openings 353 and 354 respectively proximal to electrode 350 and electrode 351 so that blood flowing in the renal vessel can flow into the catheter internal lumen at one opening and out of the internal catheter lumen back into the renal vessel at the other opening, thus providing a shunt path for blood flow even when the balloon is inflated and is occluding most of the vessel cross section. As will be described in detail below, the blood path also offers advantages in terms of distribution of electric field when a voltage difference is applied between the electrodes for pulsed high voltage delivery. In a preferred embodiment, the distal tip of the catheter can be rounded gently or tapered and rounded so as to present a smooth, blunt distal tip profile.

Figure 3:
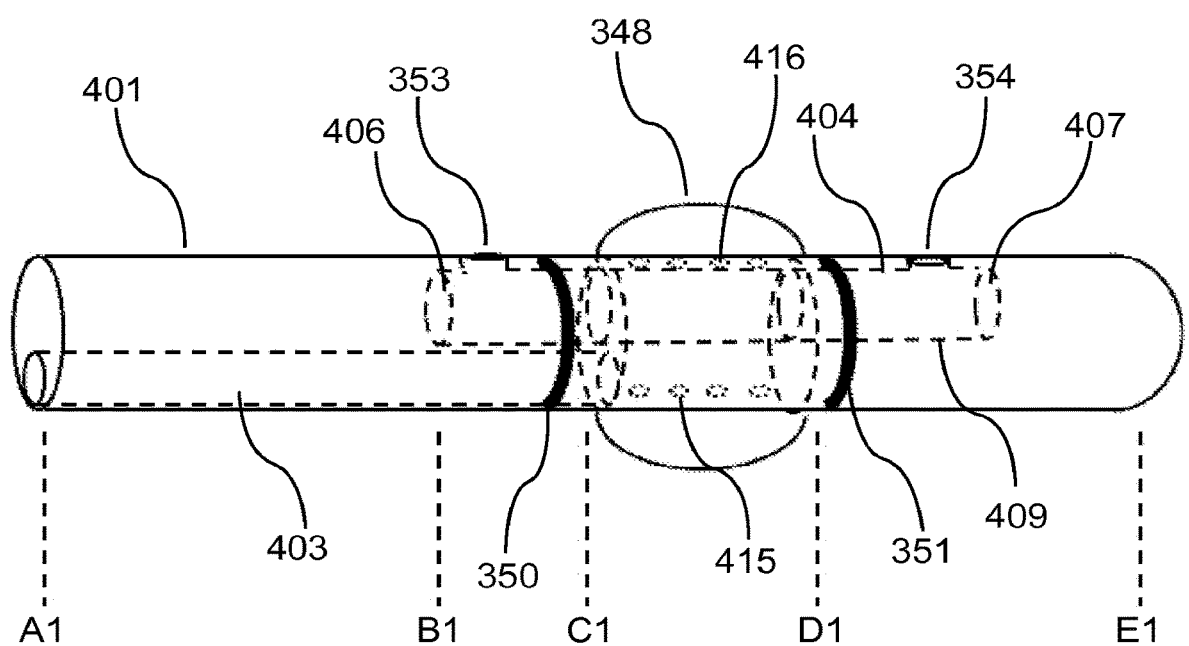
FIG. 3 is a side view of a catheter assembly according to an embodiment showing the catheter shaft, expandable member, and electrodes.

A catheter device 400 according to an embodiment is shown in a more detailed illustration (not to scale) in FIG. 3. The distal portion of the catheter shaft 401 has an inner lumen 403 that runs from the proximal catheter end (not shown) to the distal portion, for delivery of pressurized air or fluid (such as, for example, saline) that may be utilized to inflate the balloon. In the FIG., the lumen 403 starts from a cut plane or section A1 and runs up to approximately the proximal end of the balloon (denoted by section C1), where it expands to fill a larger eccentric annular space within the catheter with openings (indicated by the small dotted ellipses such as 415 and 416) on the shaft that open into the balloon. Pressurized air or fluid injected into the proximal end of the lumen 403 can thus inflate the balloon 348 in FIG. 3. Further, the catheter has a shorter inner lumen 409 providing a blood path, with ends indicated by the reference characters 406 and 407. This inner lumen has proximal and distal openings 353 and 354, respectively, to the exterior lateral surface of the catheter, so that blood (which has a flow direction in the renal vessel from proximal to distal along the catheter when the catheter is inserted into the renal vessel as indicated in FIG. 1) can enter at one opening (for example, 353), flow inside the inner lumen 409 and exit through the other opening (for example, 354).

As shown, electrodes in the form of rings 350 and 351 are indicated as mounted on the catheter shaft near proximal and distal ends respectively of the balloon 348. The electrodes 350, 351 can have any suitable size and/or shape. For example in some embodiments, the electrodes 450, 451 can be a ring-shaped electrode having a width in the range 1 mm-6 mm, and a diameter in the range of about 1 mm to about 6 mm. The nearest edge-to-edge separation between electrodes can be in the range from about 3 mm to about 25 mm.

In one method of assembly, segmental pieces A1-B1, B1-C1, C1-D1, and D1-E1 with distinct and suitably mating lumen structures can comprise polymeric material, be extruded separately and joined by processes such as heat bonding that are well known to those skilled in the art. Various polymeric materials can be used in the construction; for example, the balloon can be made of thin polyurethane with suitable stretchability (or compliance) for inflation. The catheter shaft can comprise polymers such as Teflon, polyurethane, Nylon, PEEK (Poly Ester Ester Ketone) or polyethylene that are utilized frequently in the medical device industry and known to one skilled in the art. The balloon 348 (and any of the balloons or expanded members described herein) can have a length in the range 3 mm-25 mm and an inflated diameter in the range 2 mm-6 mm. It is to be noted that in alternate embodiments, the inflatable balloon 348 (and any of the balloons or expanded members described herein) can instead be in the form of an expandable member, whether in the form of an expanded structure with a mesh-based unfolding structure, or a variety of other forms known to those skilled in the art. In the latter case the expandable member can have an expanded diameter in the range of about 2 mm to about 6 mm and a length in the range 3 mm-25 mm.

The catheter shaft can also include metallic mesh or braid constructions in the wall for torque transmission and suitable rigidity. The electrodes can include metals such as Platinum Iridium alloy, stainless steel, silver or other biocompatible metals that are known in the medical device industry as suitable electrode materials, and may be affixed to the catheter by an etching and gluing process, swaging, crimping or other processes known to one skilled in the art. The electrodes have leads attached to the inner or non-exposed side that run back to the catheter handle for connection to an appropriate electrical connector (not shown in FIG. 3). The diameter of the catheter can be in the approximate range 0.8 mm-4 mm. While the materials and methods mentioned here are for illustrative purposes, it should be appreciated that those skilled in the art can conceive of the use of a variety of other materials and construction methods.

Figure 4:
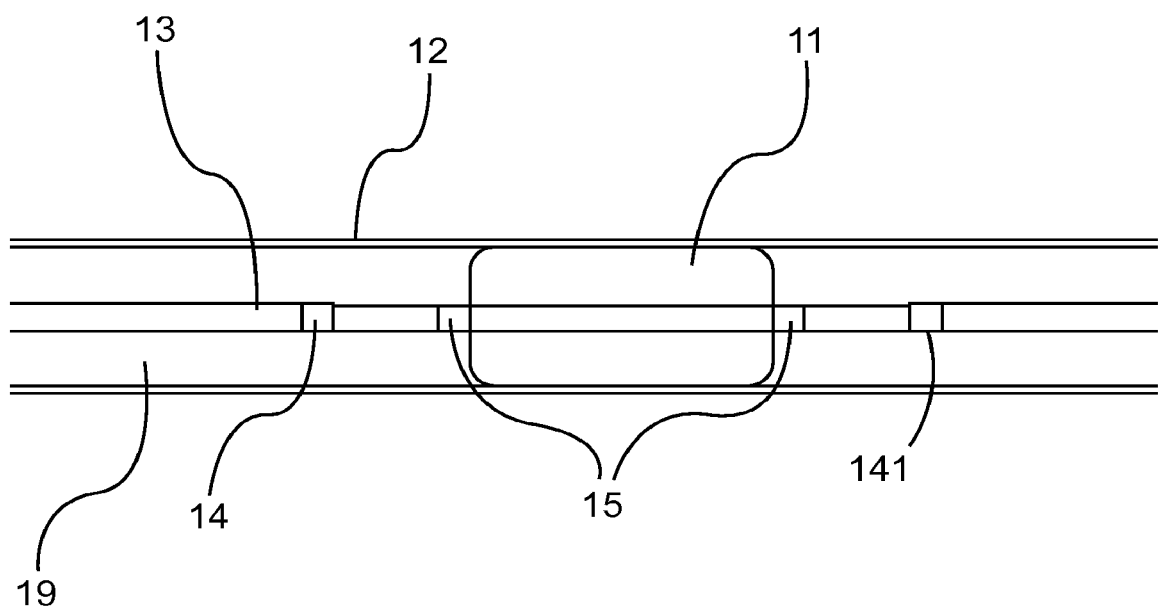
FIG. 4 is a schematic cutaway view of a catheter assembly according to an embodiment in a central longitudinal plane of the catheter with the plane passing through the longitudinal axis of the catheter, and showing the distal portion of the catheter with expanded member inside a blood vessel with a vessel wall and a blood pool in the annular space between the catheter and the vessel wall, together with blood path through the catheter.

A schematic cutaway view of a catheter 13 according to an embodiment is shown in FIG. 4 in a central longitudinal plane of the catheter with the plane passing through the longitudinal axis of the catheter, and showing the distal portion of the catheter with inflated balloon inside a blood vessel with a vessel wall and a blood pool in the annular space between the catheter and the vessel wall, together with blood path through the catheter. The distal portion of the catheter 13 has a balloon 11 disposed on it, said balloon being inflated within a renal vessel with a thin vascular wall 12. The balloon includes an electrical insulator, for example in the form of a mechanically compliant polymer such as polyurethane. Electrodes 15 on either end of the balloon can be polarized with an electrical voltage or potential difference. Flowing blood pool 19 is present in the renal vessel, enters the inner catheter lumen through opening 14 in the catheter wall and exits the inner lumen through opening 141. In use, either of the electrodes 15 can serve as anode, with the other member of the pair then taking on the role of cathode. Electrical leads (not shown) passing through a hollow lumen in the catheter connect to the respective electrodes for voltage delivery. The electrical leads are provided with suitable high dielectric strength insulation utilizing a suitable material such as for example Teflon. In some embodiments, the material and thickness of the high dielectric strength insulation is chosen so that it can withstand a voltage of at least 500 Volts in the electrical conductor of the lead without dielectric discharge or breakdown. As described herein, finite element analysis of the current density for the entire geometric region shown in FIG. 4 was conducted. In particular, the geometry shown can be used in a computational model with appropriate physical parameters (such as electrical conductivities) assigned to blood, tissue, metal and insulator to compute the electric potential and field in the spatial region around the catheter when a voltage or potential difference is applied between the electrodes.

Figure 5:
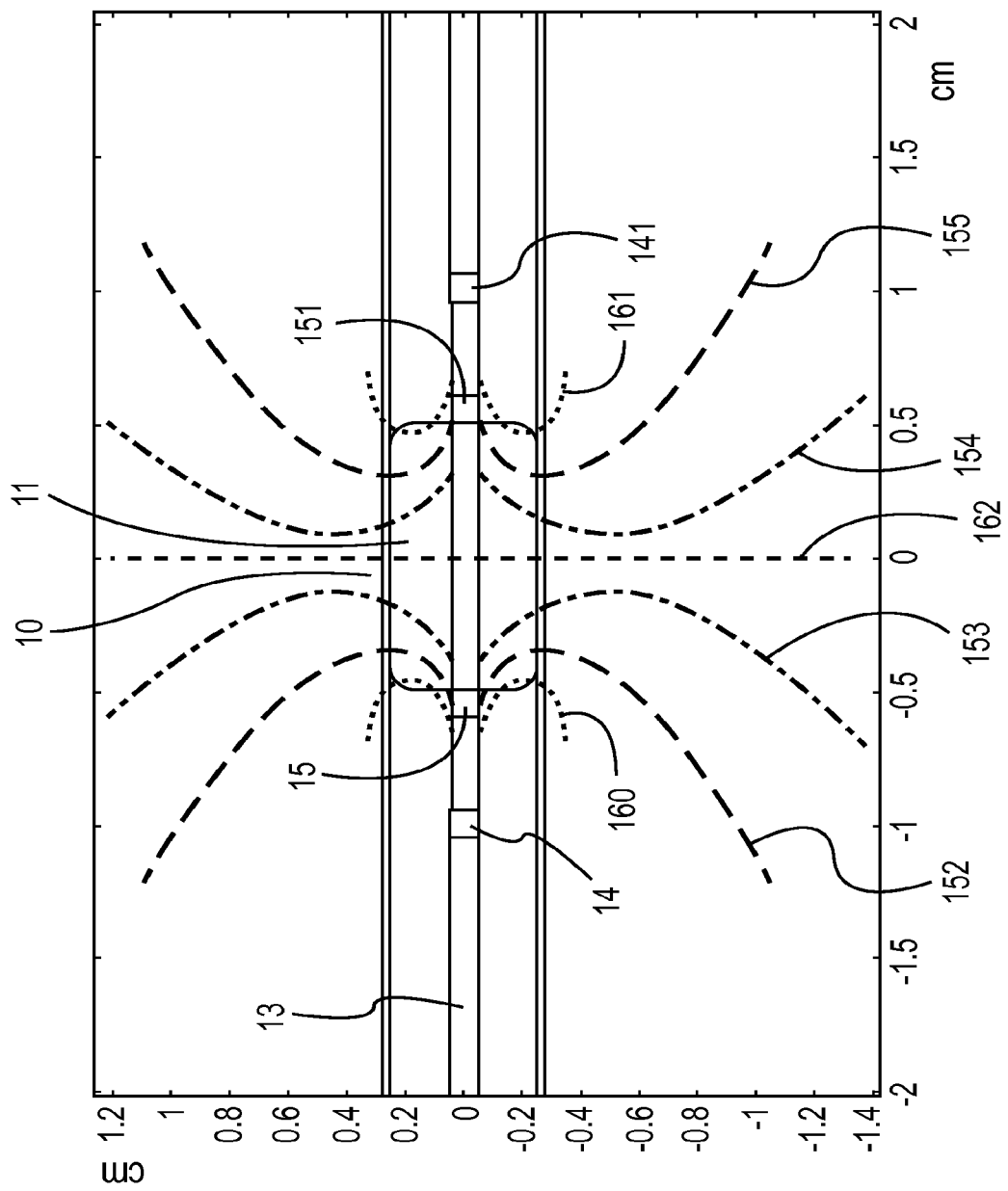
FIG. 5 illustrates a finite element analysis-derived spatial intensity plot of electric voltage or potential within a three dimensional geometry including the catheter assembly of FIG. 4 with expanded member and a blood path when a defined electric potential difference is applied between the electrodes of the catheter.

Such a simulation result is shown in FIG. 5 in the form of a shaded intensity plot for the electric potential, when the proximal electrode 15 has a high potential (500 Volts) and the distal electrode 151 is assigned a low potential (ground or zero voltage). FIG. 5 also indicates the catheter shaft 13, openings 14 and 141 in the catheter for access to the blood path, the balloon 11 and the vessel wall 10. The electric potential is directly solved for in the computational model, and its negative gradient (the electric field vector E) may be thence evaluated as well as the current density $j=\sigma E$. The indicated contours 160, 152, 153, and 162 (marked by dashed contour lines in FIG. 5) represent isopotential lines at approximate voltages of 500 Volts, 420 Volts, 320 Volts, and 250 Volts, respectively, while the dashed lines 154, 155 and 161 represent isopotential lines at voltages 180 Volts, 80 Volts, and 0 Volts, respectively.

Figure 6:
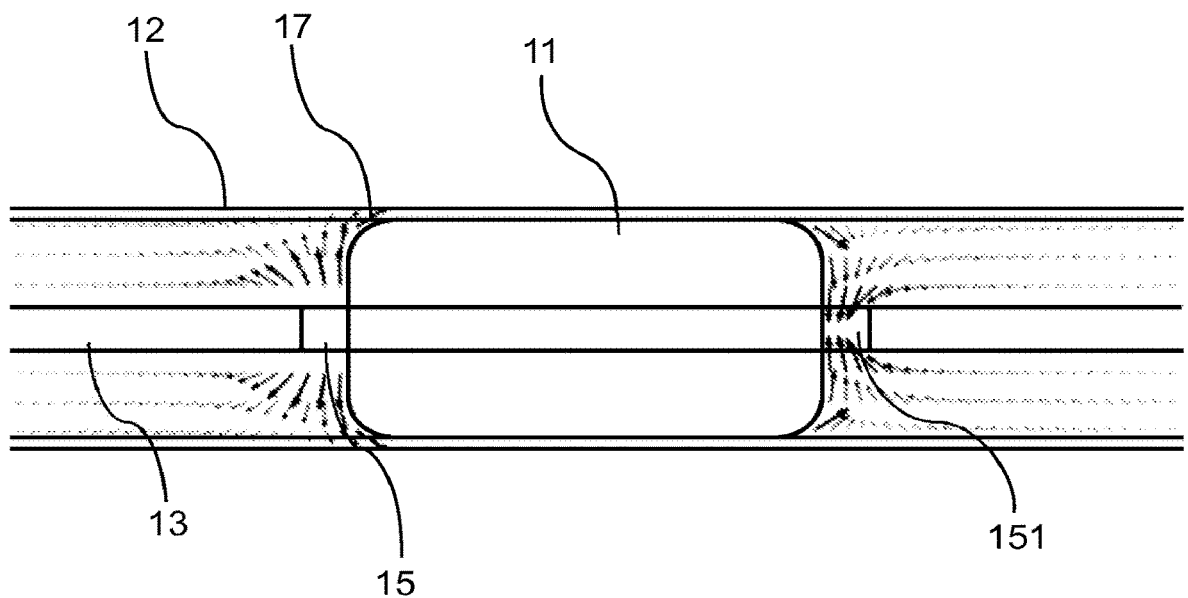
FIG. 6 depicts a finite element analysis-derived spatial quiver plot of current density within a finite element geometry similar to that of FIG. 4, but without a blood path through the catheter, when a defined electric potential difference is applied between the electrodes of the catheter.

A finite element analysis-derived spatial quiver plot of current density within a finite element geometry similar to that of FIG. 4 but without a blood path through the catheter is depicted in FIG. 6. The arrows in the quiver plot indicate the local direction of the current density vector and the arrow length indicates the magnitude of local current density when a defined electric potential difference is applied between the electrodes of the catheter, with electrode 15 at a high potential and electrode 151 at a low potential. The catheter shaft is indicated as 13 and the vessel wall 12 is also labeled in the FIG. along with the balloon 11. The current density exits electrode 15 and enters electrode 151 with the potential difference applied between the electrodes. It can be noted that there is a significant magnitude of current density 17 at or near the vessel wall, determined from the simulation to correspond to an electric field intensity or magnitude of over 1260 Volts/cm.

Figure 7:
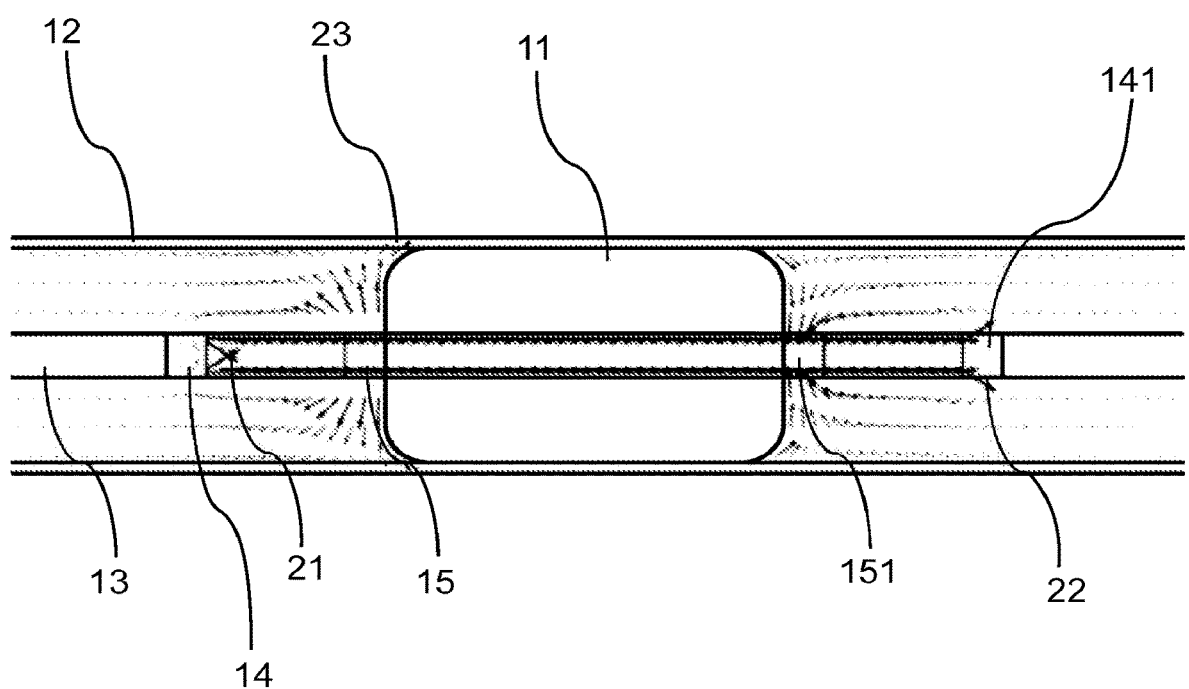
FIG. 7 depicts a finite element analysis-derived spatial quiver plot of current density within the finite element geometry of FIG. 4 including a blood path through the catheter, when a defined electric potential difference is applied between the electrodes of the catheter.

In like manner, FIG. 7 depicts a finite element analysis-derived spatial quiver plot of current density within the finite element geometry of FIG. 4 including a blood path through the catheter, again with the arrows in the quiver plot indicating the local direction of the current density vector and the arrow length indicating magnitude of local current density when a defined electric potential difference is applied between the electrodes of the catheter, with electrode 15 at a high potential and electrode 151 at a low potential. The catheter shaft is indicated as 13 and the vessel wall 12 is also labeled in the FIG. along with the balloon 11. The current density exits electrode 15 and enters electrode 151 with the potential difference applied between the electrodes. It can be noted that the magnitude of current density 23 at or near the vessel wall is now very small. Further, there is a significant current density 21 near the opening 14 flowing in the same direction as the blood flow/path and exiting at the opening 141 before it loops back to enter at electrode 151. In effect, excess current at the vessel wall has been shunted to flow through the blood path in the internal lumen of the catheter instead. Indeed, from the simulation it was determined that a peak electric field intensity or magnitude of approximately 500 Volts/cm was produced at the vessel wall. This electric field intensity is large enough to generate irreversible electroporation ablation while not being large enough to cause a local hot spot or thermal damage, in contrast to the case of the catheter device without the blood path.

Figure 8:
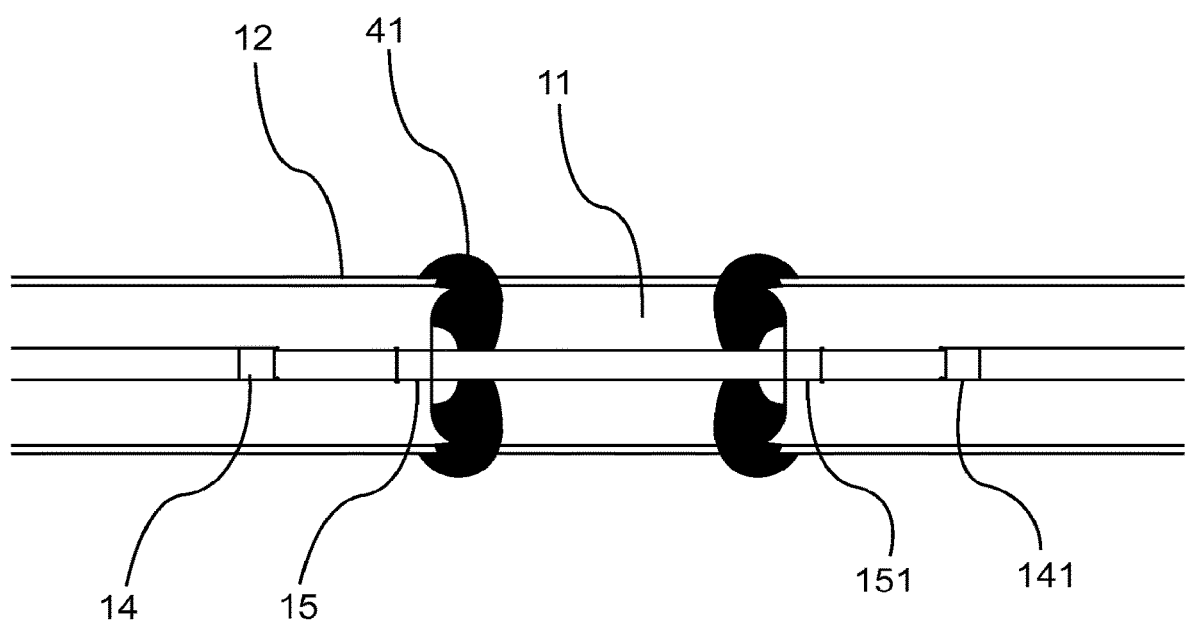
FIG. 8 illustrates a finite element analysis-derived spatial intensity plot of electric field within a three dimensional geometry including a catheter of the present invention with expanded member and a blood path, when a defined electric potential difference is applied between the electrodes of the catheter.

FIG. 8 illustrates a finite element analysis-derived spatial intensity plot of electric field within a three dimensional geometry including a catheter according to an embodiment with an inflated balloon and a blood path, the catheter placed within a blood vessel with a vessel wall and a blood pool in the annular space between the catheter and the vessel wall (i.e., the same configuration as is shown in FIG. 7). FIG. 8 shows a shaded intensity plot when a defined electric potential difference is applied between the electrodes of the catheter, with electrode 15 at a high potential and electrode 151 at a low potential. The catheter shaft is indicated as 13 and the vessel wall 12 is also labeled in FIG. 8 along with the balloon 11. The shaded area represents the region where the electric field intensity is approximately 500 V/cm, suitable for the irreversible electroporation of renal nerve endings in the vessel wall, and it can be seen as indicated by 41 that the vessel wall has an appropriate electric field intensity for ablation. Regions with very high intensity electric fields (leading to thermal hot spots) have been effectively moved away from the interior of the vessel wall. In contrast, as mentioned in the foregoing, a similar catheter device without a blood path generates electric field intensities of over 1260 Volts/cm at the vessel wall.

Figure 9A:
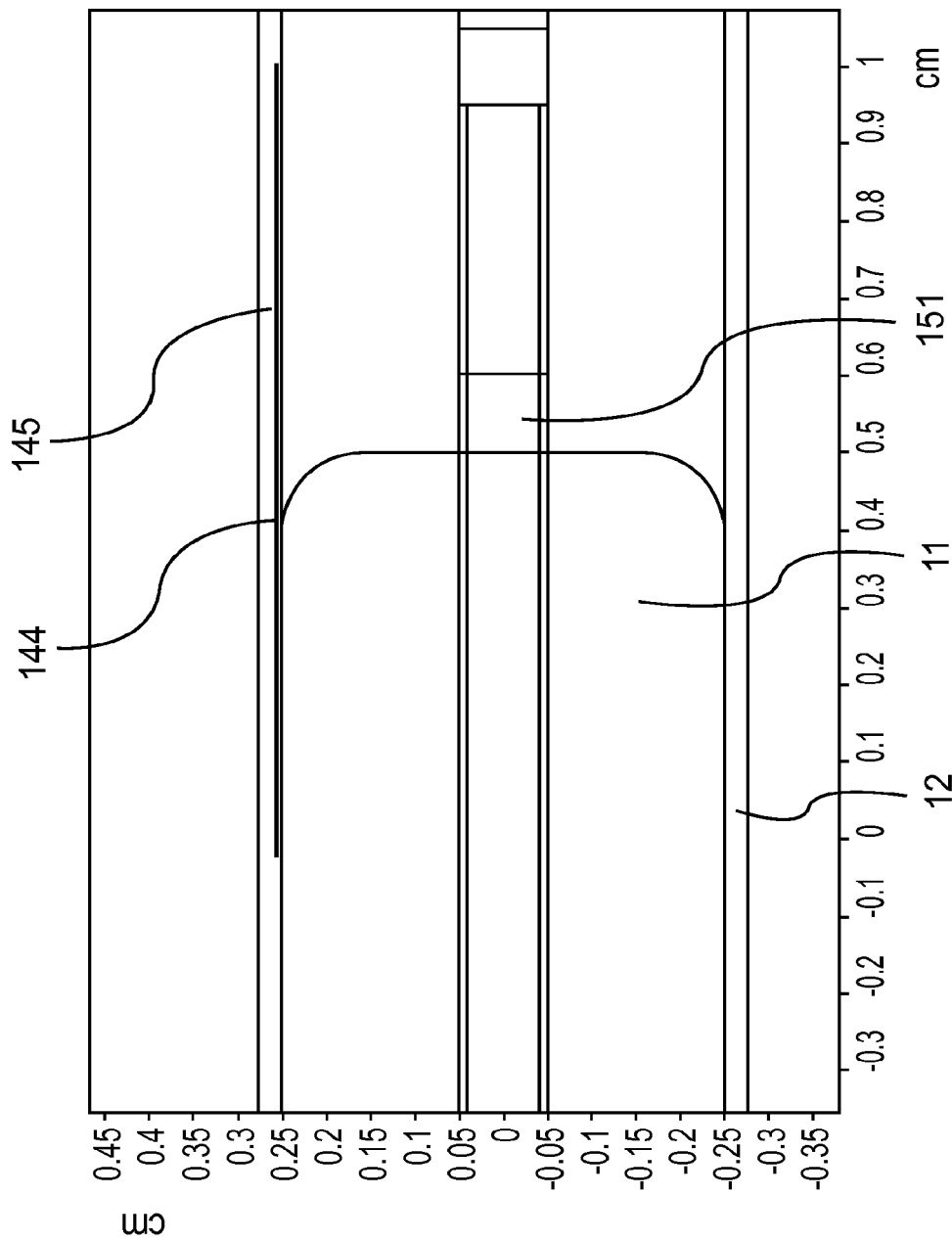
FIG. 9A is an illustration of a balloon catheter according to an embodiment in a renal vessel and showing a line segment along the inner vessel wall along which electric field intensity values can be plotted.
Figure 9B:
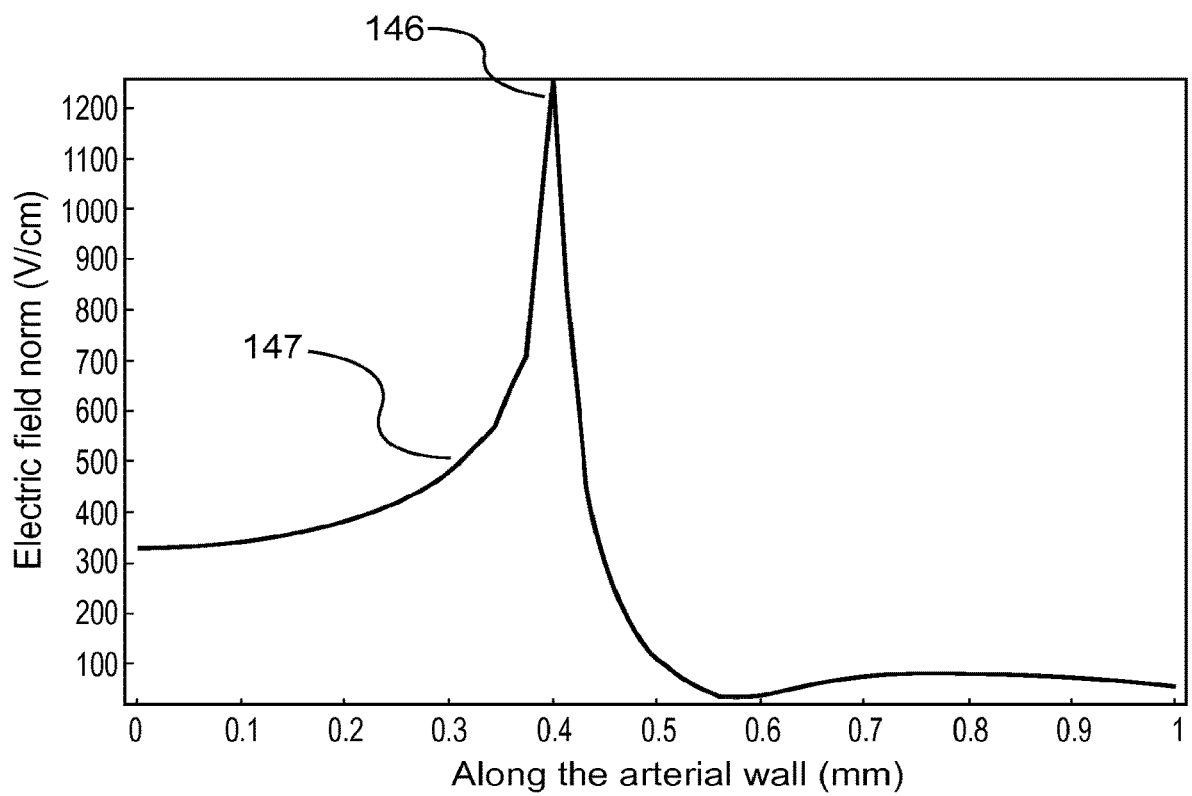
FIG. 9B is a graph plotting the variation of electric field intensity along the line segment of FIG. 9A.

The sharp drop-off of electric field intensity from a localized peak along a longitudinal direction can be illustrated with line plots as for example shown in FIGS. 9A and 9B. FIG. 9A shows a portion of the balloon catheter with balloon 11 and electrode 151 disposed in a vessel with arterial walls 12. A longitudinal line 145 of length 1 cm centered at the point of contact 144 of the balloon with the wall (and with the line 145 disposed at the inner surface of the vessel wall) is used as a line along which electric field intensity is plotted in FIG. 9B. As seen in FIG. 9B, the peak value 146 of electric field intensity along the line 145 of FIG. 9A substantially drops from a value of approximately 1200 V/cm to a value 147 of 500 V/cm within about 1 mm.

In one embodiment, the catheter has at least one anode-cathode pair of electrodes that are recessed from the exterior surface of the distal region of the catheter. With the electrodes positioned away in a radially inward manner from the diameter profile of the cross section of the catheter, the electric field generated due to an applied potential difference between the electrodes is not excessively large at the arterial wall, thus preserving the wall itself. At the same time, the nerve cells in the nerves present in the vascular wall are in the presence of an electric field large enough to generate irreversible electroporation and subsequent cell necrosis.

The recessed electrodes contact blood in the vessel, with blood thus forming a portion of the electrical path between anode and cathode electrodes. The vascular wall also forms a portion of the electrical path between anode and cathode electrodes. In some embodiments, all the electrodes on the catheter are recessed so that there is no direct physical contact between any of the electrodes and the vascular wall. Thus, the intense electric field near the electrode surface is removed from the wall, reducing or eliminating the likelihood of vessel wall perforation while the electric field is still large enough to generate irreversible electroporation of the renal nerve endings therein. In some embodiments, a pair of anode and cathode electrodes are set in a recessed void in the catheter, and separated from each other by an insulator. The voltage pulses can for exemplary purposes have pulse widths in the range of tens to hundreds of microseconds. In some embodiments there could be a multiplicity of such voltage pulses applied through the electrodes, with an interval between pulses that can for illustrative purposes be in the range of tens to hundreds of microseconds. The generator can output waveforms that can be selected to generate a sequence of voltage pulses in either monophasic or multiphasic forms and with either constant or progressively changing amplitudes.

Figure 10:
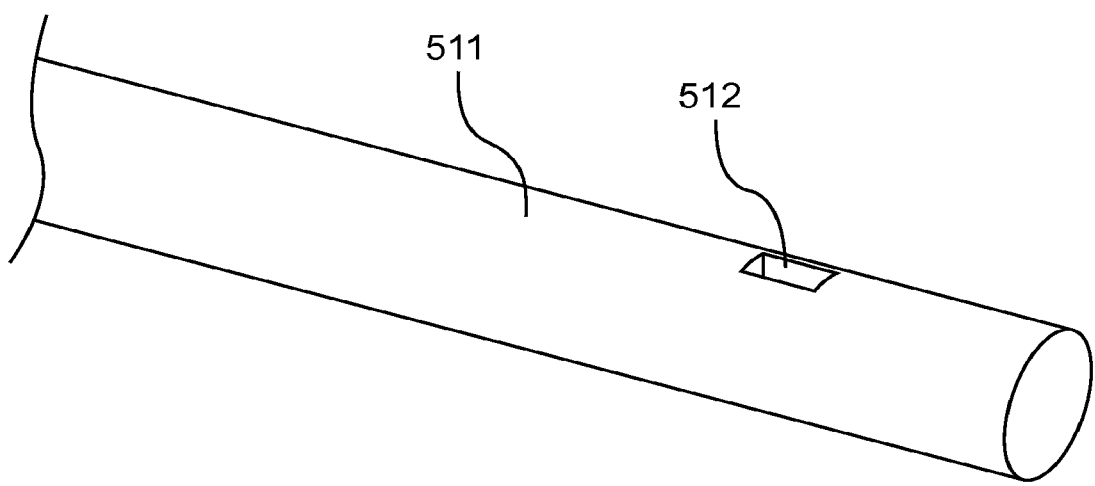
FIG. 10 is an illustration of a catheter embodiment showing a recessed void in the exterior surface of the catheter wherein electrodes are disposed.

A catheter according to an embodiment having a recessed void in the exterior surface of the catheter, wherein recessed electrodes are disposed therein for applying electrical voltages for ablation purposes, is shown in FIG. 10. As shown, the distal portion 511 of the catheter body has a recessed void 512 where electrodes are located, with anode and cathode electrodes on diametrically opposite sides of the catheter's central longitudinal axis. In some embodiments, the distal tip of the catheter can be rounded gently or tapered and rounded (not shown in FIG. 10) so as to present a smooth, blunt distal tip profile.

Figure 11:
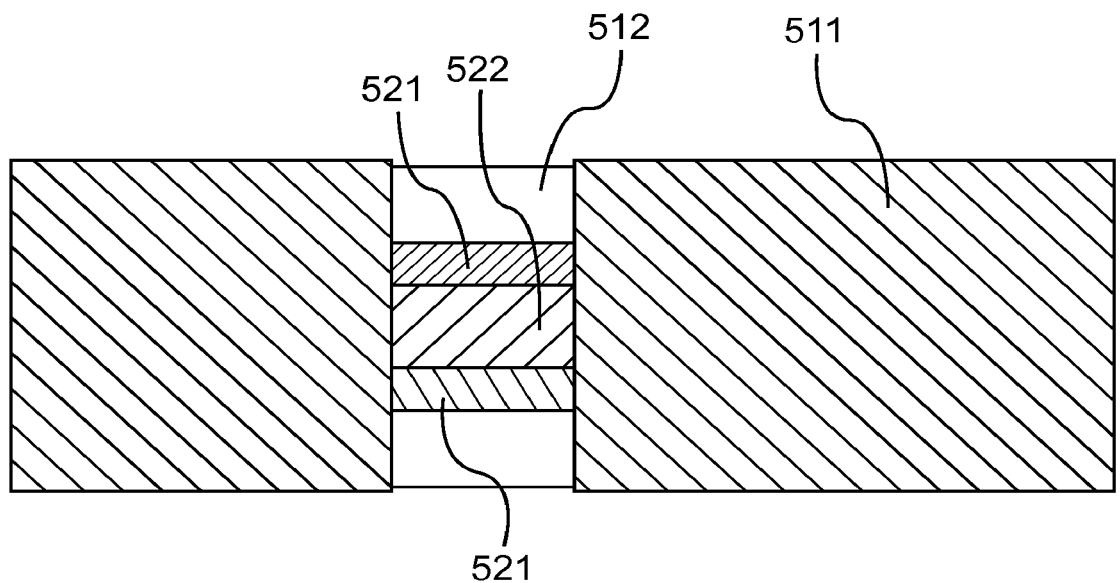
FIG. 11 is a schematic cross-sectional view of a catheter embodiment in a central longitudinal plane of the catheter with the plane passing through the longitudinal axis of the catheter.

The internal arrangement of the electrodes within the recess is displayed more clearly in FIG. 11, which shows a schematic cross-sectional view of a catheter 511 in a central longitudinal plane of the catheter with the plane passing through the longitudinal axis of the catheter. As shown, the catheter body 511 has a recess or void 512, within which are located metallic or electrically conducting electrodes 21 disposed on either side of an electrical insulator 522. The catheter body can be made of Teflon, polyurethane, Nylon, PEEK (Polyether Ether Ketone), polyethylene or any of a range of polymers commonly used in the medical device industry to build catheter devices and known to those skilled in the art. The diameter of the catheter can be in the approximate range 0.8 mm-4 mm. The void or recess can have a length dimension in the range 0.5 mm-5 mm and a width dimension in the range 0.2 mm-2 mm at the exterior catheter surface, while having a recess or depth dimension in the approximate range 0.5 mm-1.5 mm measured radially inward from the surface. The ratio of recess depth to catheter diameter can be in the range 0.1 to 0.45. The metallic electrodes can comprise biocompatible materials such as platinum iridium, stainless steel, silver or a range of other conductors familiar to one skilled in the art. The void can be fabricated by machining, drilling, punching or molding. The insulator between the electrodes can comprise materials such as Teflon or polyurethane that are known to have a high dielectric strength. The electrodes and insulator between the electrodes can be positioned by etching the catheter and held in place by a suitable gluing process.

It is to be noted that while FIG. 11 shows a rectangular geometry for the electrodes and flat surfaces for the recess walls, more general shapes could be used in other embodiments. Thus for example ellipsoidal electrodes disposed in a recess with either flat or curved walls, approximately spherical or ellipsoidal recess walls, and so on can be used in some embodiments. In one embodiment, approximately rectangular parallelepiped electrodes are disposed in the catheter, with edges and corners rounded to result in gently curving forms in order to reduce or eliminate areas of high curvature, which can result in further reductions in electric field intensity distributions.

Figure 12:
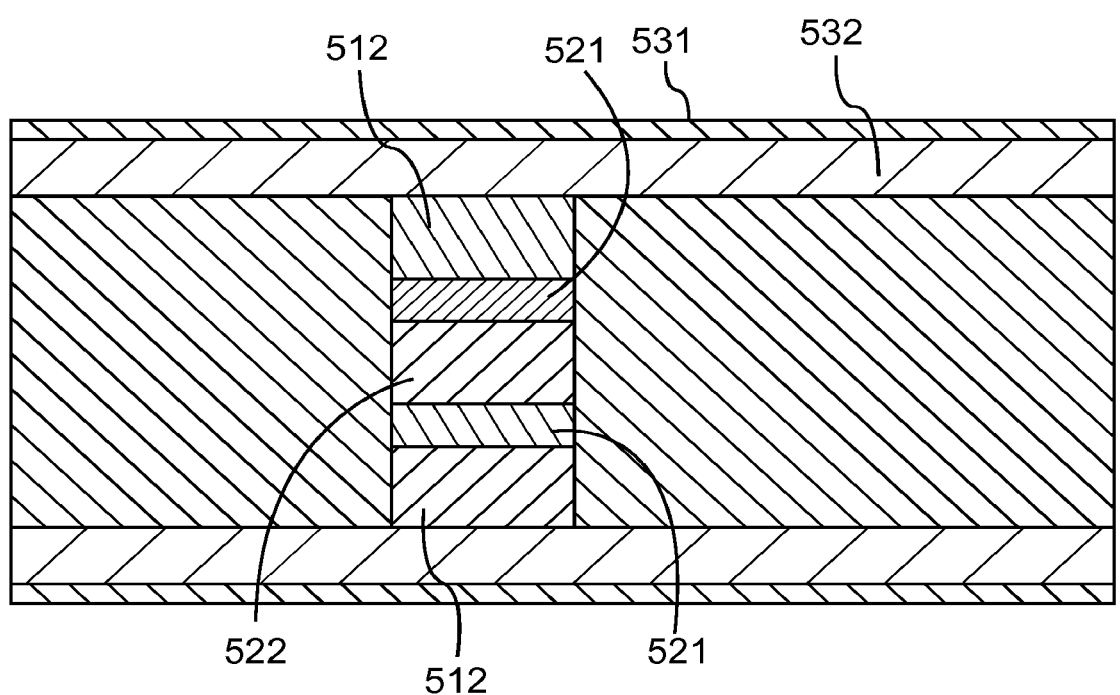
FIG. 12 is a schematic cross-sectional view of the catheter shown in FIG. 11 disposed inside a blood vessel with a vessel wall.

FIG. 12 illustrates a schematic cutaway view of a catheter according to an embodiment along a central longitudinal plane of the catheter with the plane passing through the longitudinal axis of the catheter, and showing the catheter inside a blood vessel with a vessel wall 531 and a blood pool 532 disposed in the annular space between the catheter and the vessel wall, together providing a geometry for finite element analysis. The recess or void 512 in the catheter body, and the electrically conducting electrodes 521 within the void are indicated along with the electrical insulator 522 disposed between the electrodes 521. In use, either of the electrodes 521 can serve as anode, with the other member of the pair then taking on the role of cathode. Electrical leads (not shown) passing through a hollow lumen in the catheter connect to the respective electrodes for voltage delivery. The electrical leads are provided with suitable high dielectric strength insulation utilizing a suitable material such as for example Teflon; the material and thickness of the high dielectric strength insulation is chosen so that it can withstand a voltage of at least 500 Volts in the electrical conductor of the lead without dielectric discharge or breakdown. In an alternate embodiment, the high dielectric strength insulation is chosen so that it can withstand a voltage of at least 2000 Volts in the electrical conductor of the lead without dielectric discharge or breakdown.

Figure 13:
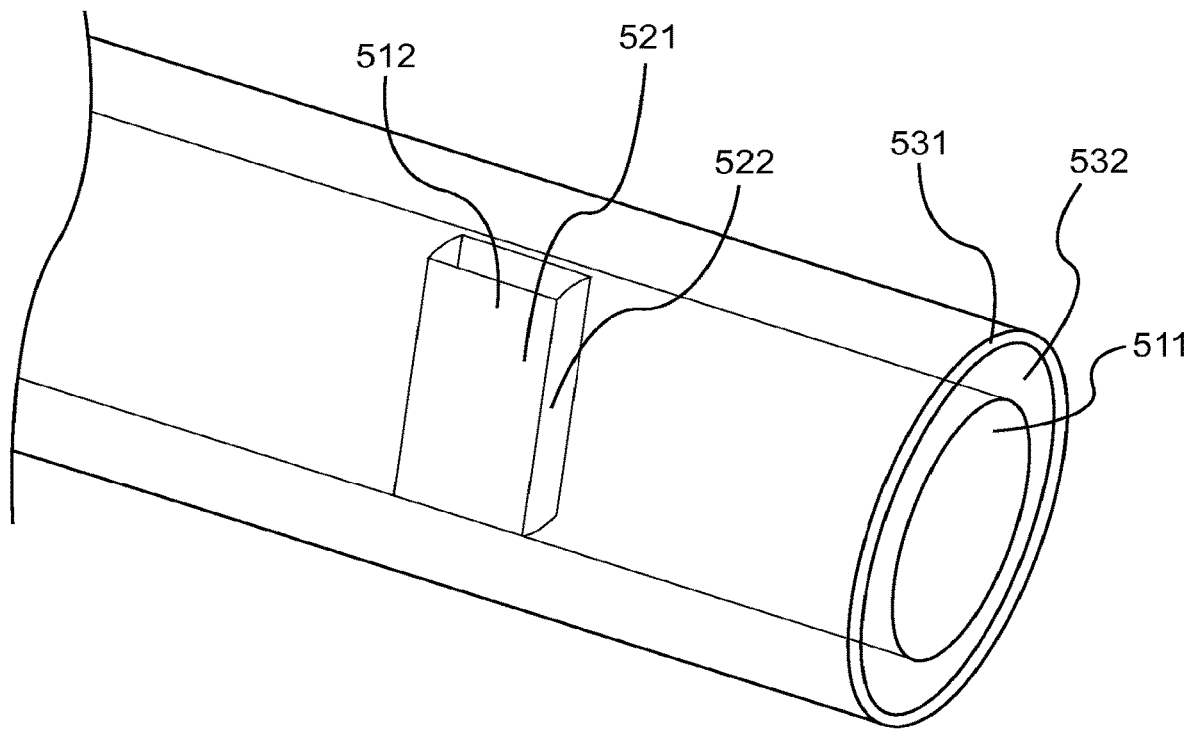
FIG. 13 illustrates the three dimensional geometry of a catheter embodiment with recessed electrodes, the catheter placed within a blood vessel with a vessel wall and a blood pool in the annular space of the blood vessel.

The three dimensional geometry of the catheter with the recessed electrodes within a blood vessel filled with blood is further illustrated in FIG. 13, where the inner cylinder represents the catheter shaft 511 within a blood vessel illustrated by vessel wall 531 and with blood 532 disposed in the annular space between the catheter shaft and the vessel wall. The electrodes 512 and insulator 522 between the electrodes are indicated within the catheter body. This geometry can be used in a computational model with appropriate physical parameters (such as electrical conductivities) assigned to blood, tissue, metal and insulator to compute the electric potential and field in the spatial region around the catheter when a voltage or potential difference is applied between the electrodes.

Figure 14:
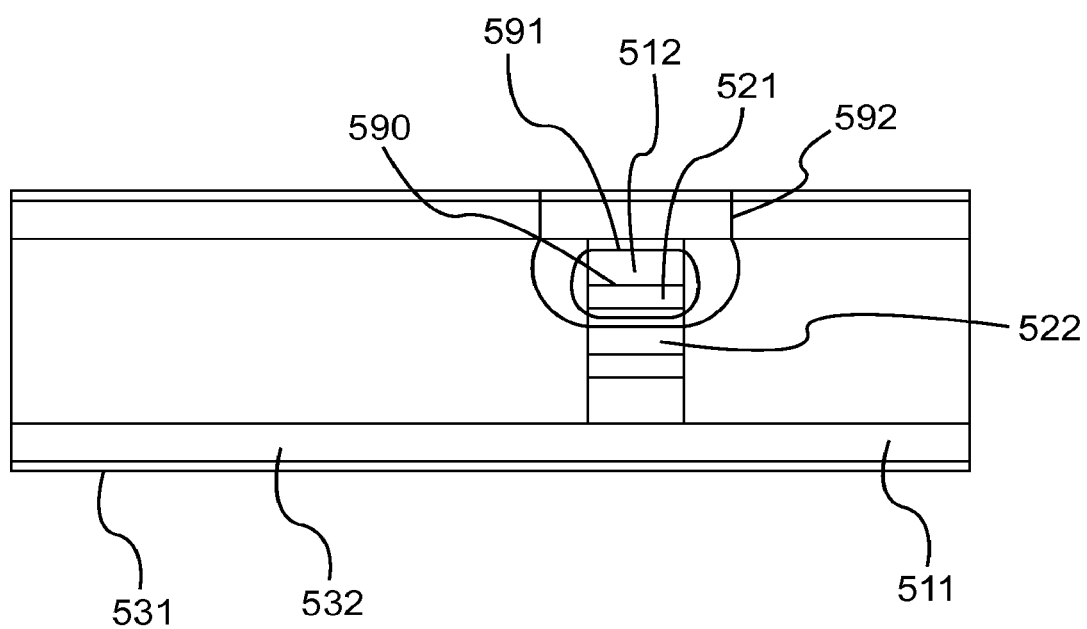
FIG. 14 illustrates a finite element analysis-derived spatial intensity plot of electric voltage within a catheter according to an embodiment.
Figure 15:
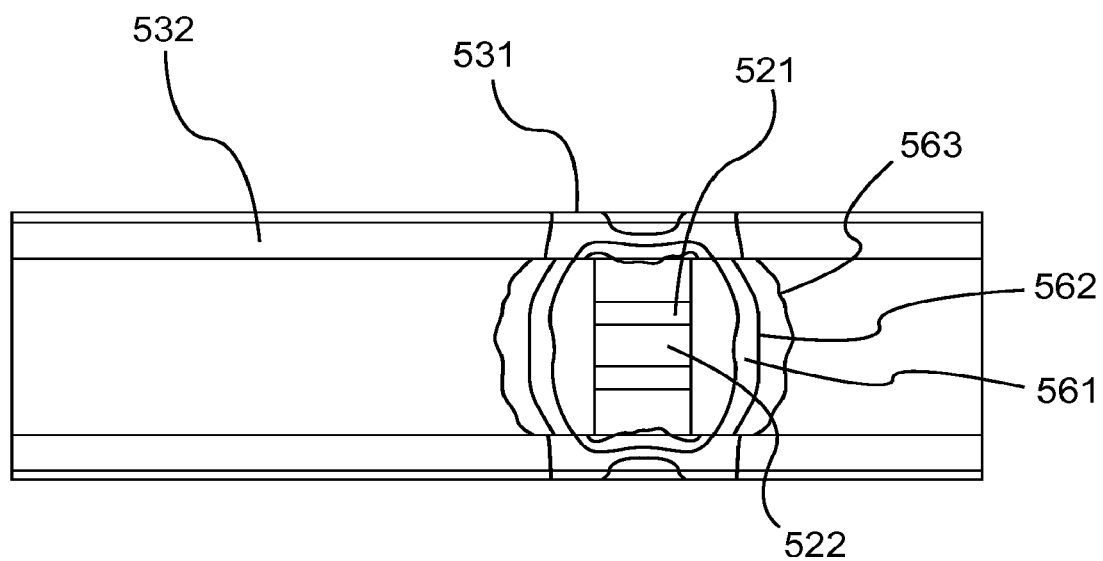
FIG. 15 depicts a finite element analysis-derived spatial intensity plot of electric field within a catheter according to an embodiment when a defined electric potential difference is applied between the electrodes of the catheter.
Figure 16:
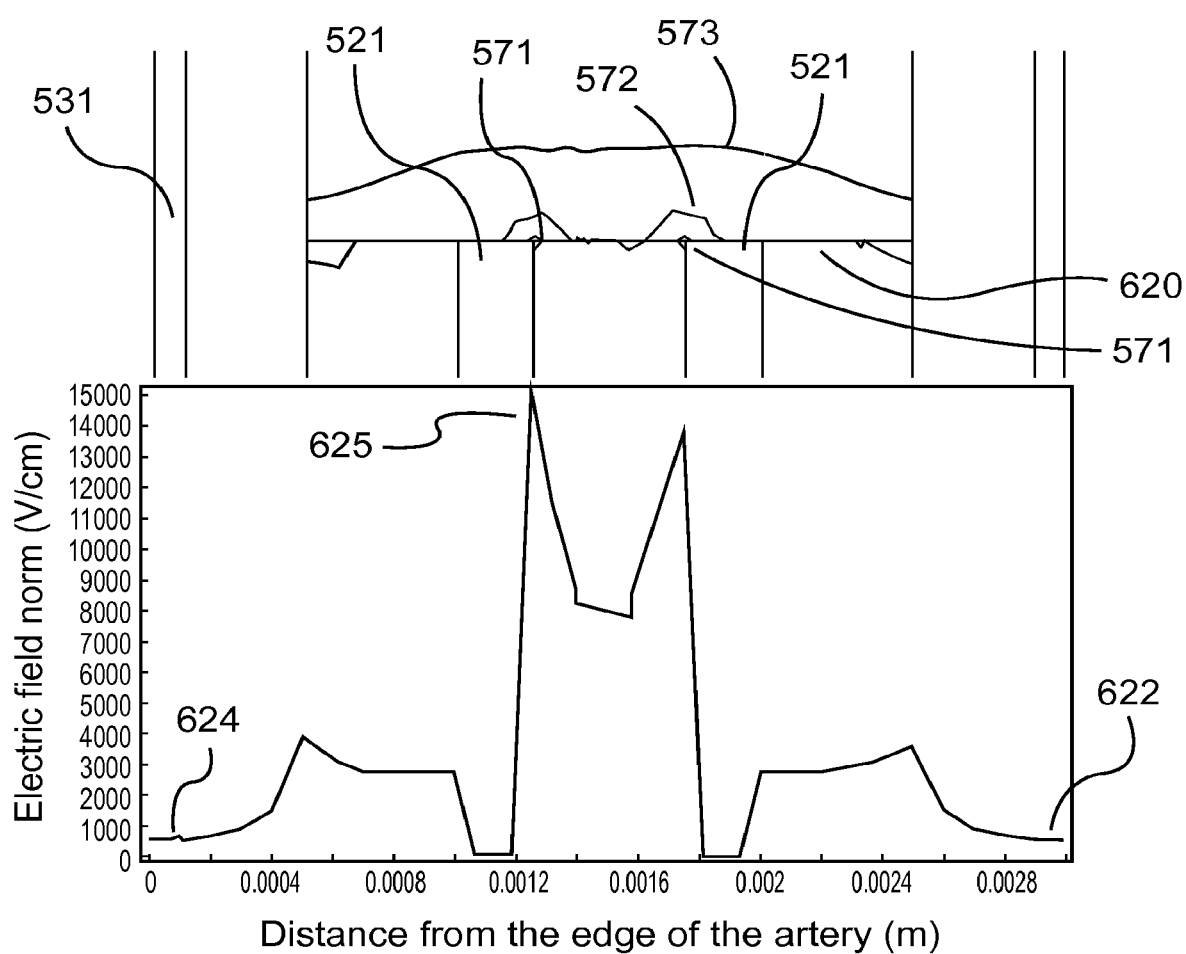
FIG. 16 shows a line plot of electric field intensity along a line perpendicular to the longitudinal axis of the catheter and passing along a transverse edge of one of the recessed catheter electrodes.

Such a simulation result is shown in FIG. 14 in a longitudinal section view in the form of a contour plot for the electric potential, when the top electrode 521 in the FIG. is assigned a high potential and the bottom electrode is assigned a low potential. In this example the high and low potentials were set at 500 Volts and zero respectively. The electric potential was directly solved for in the computational model, and its negative gradient (the electric field vector) was evaluated. In FIG. 14, contours 590, 591 and 592 correspond to isopotential lines at 500 Volts, 400 Volts and 300 Volts respectively. The magnitude of the electric field, or the electric field intensity is displayed in FIG. 15 in a longitudinal section view, also in the form of a contour plot. This plot shows electric field intensity contours 561, 562 and 563 at magnitudes of 2000 Volts/cm, 1000 Volts/cm and 500 Volts/cm respectively. It can be seen that there are high intensity electric fields 561 (approximately 2000 Volts/cm) near corners of the recess at the catheter surface, whereas outside the catheter, and in regions 531 in the arterial vessel wall, the electric field intensity 563 is significantly lower (approximately 500 Volts/cm). Thus, the very high electric field regions have been effectively moved away from the vessel wall. The electric field distribution with the same potential difference of 500 Volts between the electrodes is further clarified in FIG. 16, which provides a line plot of electric field intensity along a line perpendicular to the catheter's longitudinal axis and along one of the transverse edges of the electrodes. The plot therein shows the line plot along line 620, with the top portion of the FIG. (above the peaks in the plot) representing a rotated version of a portion of the contour plot of FIG. 15. Thus electrodes 521 are visible along with arterial wall 531 (now running in the vertical direction in the top portion of FIG. 16). Locally very high electric field intensity regions near internal corners of the electrodes are marked as contour 571 (corresponding to an electric field magnitude of approximately 14,000 Volts/cm). Contours 572 and 573 correspond to electric field magnitudes of approximately 8,600 Volts/cm and 2,900 Volts/cm respectively. Proceeding along line 620 from left to right in the FIG., the graphical plot in the lower portion of FIG. 16 shows that the electric field intensities 624 and 622 at the arterial wall are substantially reduced (they have an approximate value of 500 Volts/cm, a safe level in tissue) in comparison with the peak value 625 that occurs near inner corners of the electrode. In particular, the electric field in the tissue wall of the vessel is large enough to generate irreversible electroporation therein without being large enough to cause a thermal hot spot.

Figure 17:
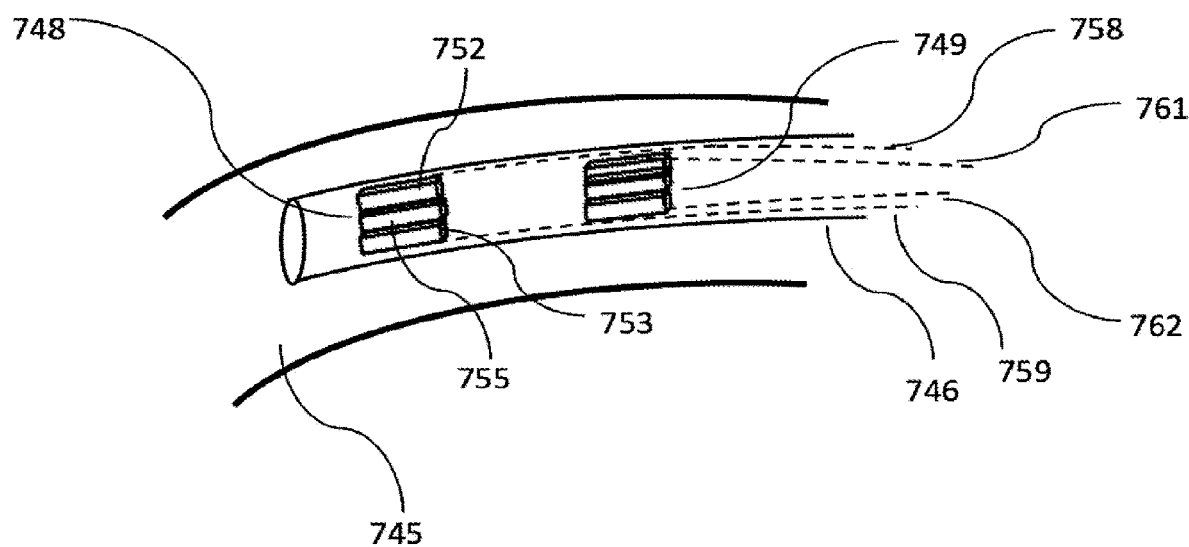
FIG. 17 shows a catheter device according to an embodiment with a multiplicity of anode-cathode electrode sets disposed along a distal length of device.

An embodiment of the catheter device according to an embodiment with two pairs of anode-cathode ablation electrodes in the distal portion of the device is illustrated in FIG. 17, which shows the distal portion 746 of the catheter device within a renal artery 745. While two pairs or sets of electrodes are shown in this illustration, in other embodiments, any number of electrodes can be disposed in the device without limitation. FIG. 17 shows a distal electrode set 748 with electrodes 752 and 753 separated by an electrically insulating region 755. Also shown is a proximal electrode set 749. Electrical leads 758 and 759 connect to electrodes 752 and 753 respectively while electrical leads 761 and 762 connect to respective electrodes of electrode set 749. The electrical leads are provided with suitable high dielectric strength insulation utilizing a suitable material such as for example Teflon; the material and thickness of the high dielectric strength insulation is chosen so that it can withstand a voltage of at least 500 Volts in the electrical conductor of the lead without dielectric discharge or breakdown. In an alternate embodiment the high dielectric strength insulation is chosen so that it can withstand a voltage of at least 2000 Volts in the electrical conductor of the lead without dielectric discharge or breakdown.

Figure 18:
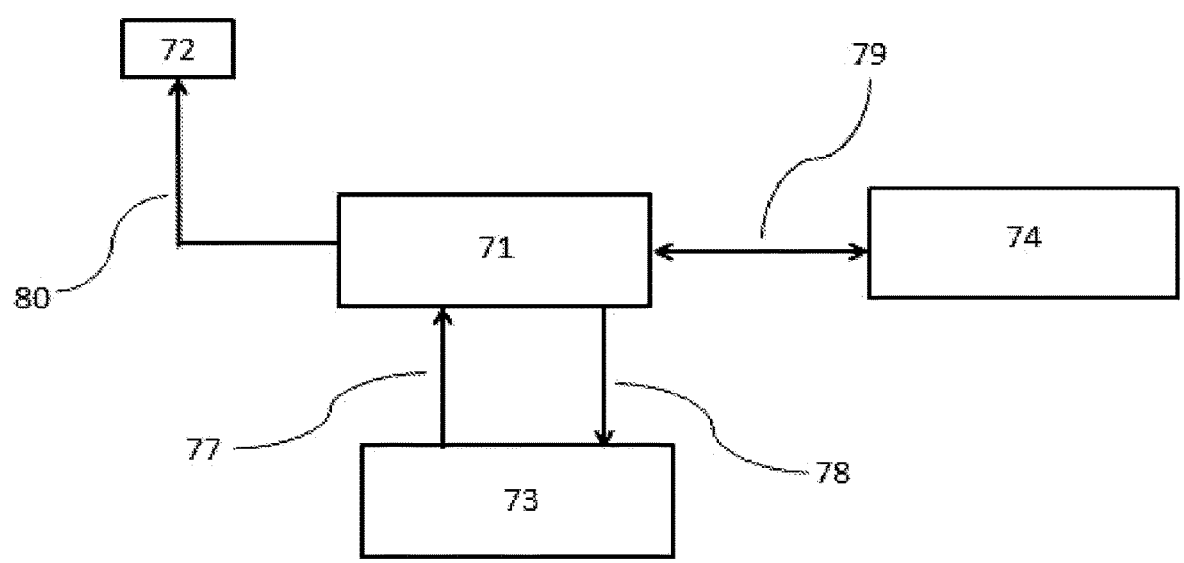
FIG. 18 schematically represents an irreversible electroporation system that together with a catheter device disclosed herein provides a therapeutic system for renal denervation ablation.

A schematic representation of an irreversible electroporation system is depicted in FIG. 18, and together with the catheter device disclosed herein it provides a complete therapeutic system for renal denervation ablation. A DC voltage/signal generator 73 is driven or triggered by a controller unit 71 that interfaces with a computer device 74 by means of a two-way communication link 79. The controller can perform channel selection and routing functions for applying DC voltages to appropriate electrodes that have been selected by a user or by the computer 74, and apply the voltages via a multiplicity of leads (shown collectively as 80) to a catheter device 72. In one embodiment the controller can also record and display impedance data from at least a pair of the electrodes of the catheter device 72. Such impedance data could for instance be used to determine suitable arterial locations for ablation. While the DC voltage generator 73 sends a DC voltage to the controller 71 through high voltage leads 77, the voltage generator is triggered by control and timing inputs 78 from the controller unit 71. In one preferred embodiment the computer 74 is integrated with the controller 71 in a single enclosure. A user interface for the system can comprise multiple elements such as, for non-limiting purposes, a graphical display, a push button, foot pedal or joystick for user-triggered ablation application, a touch screen interface, or any of a variety of such interfaces that are familiar to those skilled in the art and as may be convenient for implementation and for user interaction in the context of the medical application.

A DC voltage for electroporation can be applied to the catheter electrodes. The DC voltage is applied in brief pulses sufficient to cause irreversible electroporation can be in the range of 0.5 kV to 10 kV and more preferably in the range 1 kV to 4 kV, so that an appropriate threshold electric field is effectively achieved in the renal nerve tissue to be ablated. In one embodiment of the invention, the electrodes marked for ablation can be automatically identified, or manually identified by suitable marking, on an X-ray or fluoroscopic image obtained at an appropriate angulation that permits identification of the geometric distance between anode and cathode electrodes, or their respective centroids. In one embodiment, the DC voltage generator setting for irreversible electroporation is then automatically identified by the electroporation system based on this distance measure. In an alternate embodiment, the DC voltage value is selected directly by a user from a suitable dial, slider, touch screen, or any other user interface. The DC voltage pulse results in a current flowing between the anode and cathode electrodes, with said current flowing through the blood in the renal artery, the blood path through the catheter lumen, and the vessel wall tissue, with the current flowing from the anode and returning back through the cathode electrode. The forward and return current paths (leads) are both inside the catheter.

Figure 19:
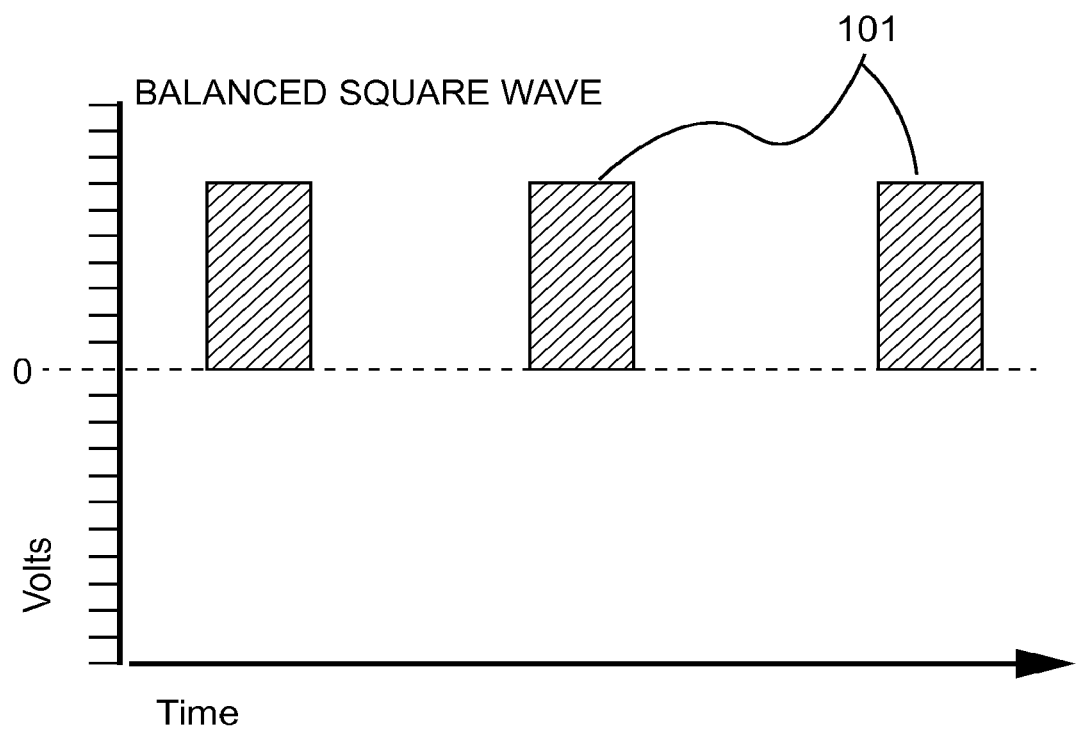
FIG. 19 is a schematic illustration of a waveform generated by the irreversible electroporation system that can be used with a catheter device disclosed herein, showing a balanced square wave.
Figure 20:
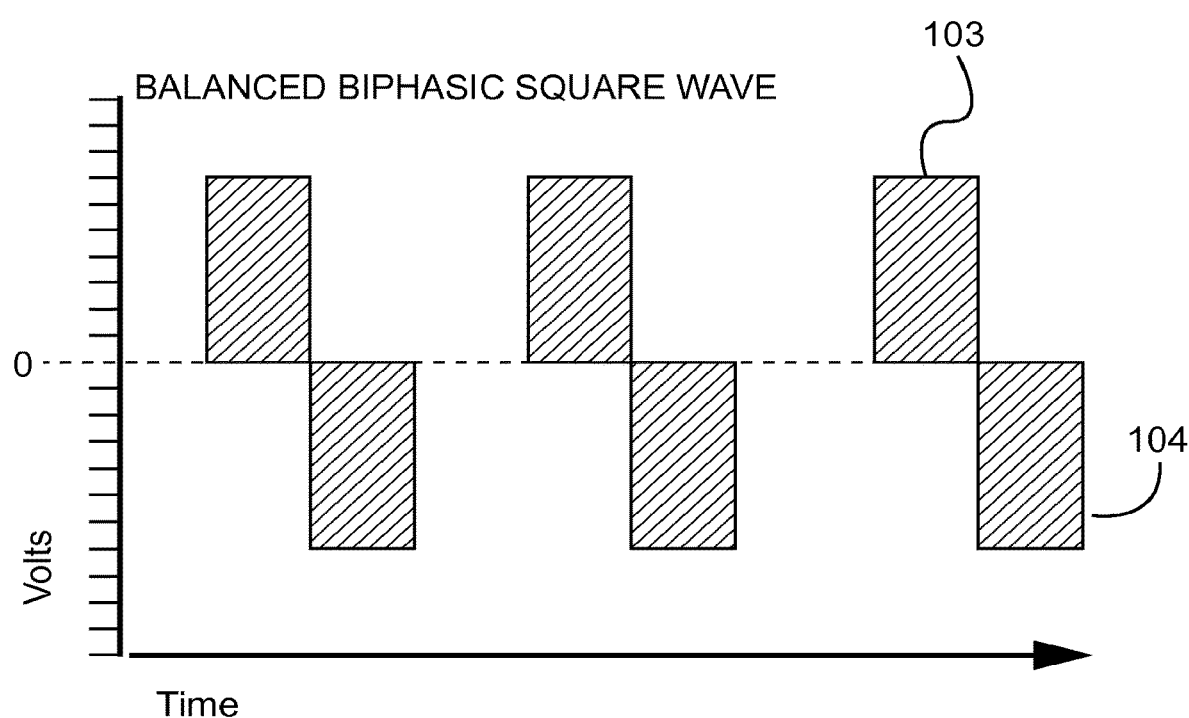
FIG. 20 is a schematic illustration of a waveform generated by the irreversible electroporation system that can be used with a catheter device disclosed herein, showing a balanced biphasic square wave.

The controller and generator can output waveforms that can be selected to generate a sequence of voltage pulses in either monophasic or biphasic or more generally, multiphasic forms and with either constant or progressively changing amplitudes. FIG. 19 shows a rectangular wave pulse train where the pulses 101 have a uniform height or maximum voltage. FIG. 20 shows an example of a balanced biphasic rectangular pulse train, where each positive voltage pulse such as 103 is immediately followed by a negative voltage pulse such as 104 of equal amplitude and opposite sign. While in this example the biphasic pulses are balanced with equal amplitudes of the positive and negative voltages, in other embodiments an unbalanced biphasic waveform could also be used as may be convenient for a given application.

Figure 21:
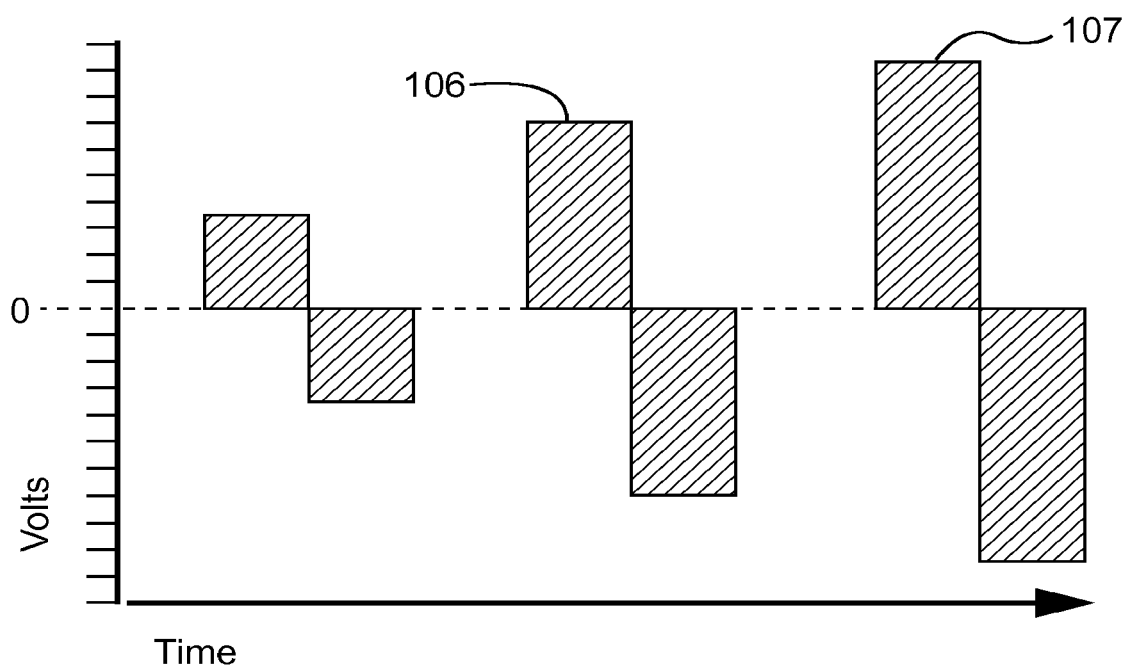
FIG. 21 is a schematic illustration of a waveform generated by the irreversible electroporation system that can be used with a catheter device disclosed herein, showing a progressive balanced biphasic square wave.

Yet another example of a waveform or pulse shape that can be generated by the system is illustrated in FIG. 21, which shows a progressive balanced rectangular pulse train, where each distinct biphasic pulse has equal-amplitude positive and negative voltages, but each pulse such as 107 is larger in amplitude than its immediate predecessor 106. Other variations such as a progressive unbalanced rectangular pulse train, or indeed a wide variety of other variations of pulse amplitude with respect to time can be conceived and implemented by those skilled in the art based on the teachings herein.

The time duration of each irreversible electroporation rectangular voltage pulse could lie in the range from 1 nanosecond to 10 milliseconds, with the range 10 microseconds to 1 millisecond being more preferable and the range 50 microseconds to 300 microseconds being still more preferable. The time interval between successive pulses of a pulse train could be in the range of 1 nanosecond to 1 millisecond, with the range 50 microseconds to 300 microseconds being more preferable. The number of pulses applied in a single pulse train (with delays between individual pulses lying in the ranges just mentioned) can range from 1 to 100, with the range 1 to 10 being more preferable. In one embodiment, a pulse train can be driven by a user-controlled switch or button, in one embodiment mounted on a hand-held joystick-like device while in an alternate embodiment it could be in the form of a foot pedal and in still another embodiment it could be implemented with a computer mouse. Indeed a variety of such triggering schemes can be implemented by those skilled in the art, as convenient for the application and without departing from the scope of the present invention. In one mode of operation a pulse train can be generated for every push of such a control button, while in an alternate mode of operation pulse trains can be generated repeatedly for as long as the user-controlled switch or button is engaged by the user.

While several specific examples and embodiments of systems and tools for tissue ablation with irreversible electroporation were described in the foregoing for illustrative and purposes, it should be clear that a wide variety of variations and alternate embodiments could be conceived or constructed by those skilled in the art based on the teachings of the present invention. Persons skilled in the art would recognize that any of a wide variety of other control or user input methods and device variations can be implemented without departing from the scope of the embodiments described herein. Likewise, while the foregoing described specific tools or devices for more effective and selective DC voltage application for irreversible electroporation, other device constructions and variations could be implemented by one skilled in the art by employing the principles and teachings disclosed herein without departing from the scope of the present invention. For example, while the description above discussed one electrode located proximal to the balloon and another electrode located distal to the balloon, in one variation a multiplicity of electrodes could be located proximal to the balloon and a multiplicity of electrodes could be located distal to the balloon.

Although various embodiments have been described as having particular features and/or combinations of components, other embodiments are possible having a combination of any features and/or components from any of embodiments as discussed above. For example, in some embodiments, a device can include an expandable member similar to the expanded member shown and described with reference to FIGS. 2 and 3 along with a recessed electrode similar to the recessed electrodes shown and described with reference to FIGS. 11 through 13.

The invention claimed is:

1. A method, comprising:
    inserting a distal end portion of a catheter shaft into a renal artery with a vessel wall, the distal end portion of the catheter shaft defining a recess, the distal end portion of the catheter shaft including a first electrode and a second electrode, each of the first electrode and the second electrode including an electrically conductive portion that is disposed below an outer surface of the catheter shaft within the recess, the catheter shaft including an electrical insulator disposed between the electrically conductive portions of the first electrode and the second electrode in the recess; and
    applying a voltage pulse train to the first electrode and the second electrode.

2. The method of claim 1, further comprising recording impedance data from the first and second electrodes.

3. The method of claim 1, wherein:
    applying the voltage train produces a voltage difference between the first and second electrodes of at least about 500 Volts,
    each of the first and second electrodes being coupled to a different insulated electrical lead including an insulation layer having a thickness and a dielectric strength configured to withstand a voltage of at least about 2000 Volts without dielectric breakdown.

4. The method of claim 1, wherein applying the voltage pulse train to the first and second electrode generates an electric field that causes irreversible electroporation of renal nerve endings near the renal artery.

5. The method of claim 1, where the catheter shaft is progressively inserted to access a multiplicity of locations along a renal artery, with the step of applying the voltage pulse train being repeated at each of said locations.

6. The method of claim 1, further comprising transitioning, prior to applying the voltage pulse train, an expandable member disposed about the catheter shaft to an expanded configuration to center the distal end portion of the catheter shaft in the renal artery.

7. The method of claim 1, wherein the catheter shaft defines a blood pathway that extends through the expandable member, the voltage pulse train being applied to the first and second electrodes while the pathway shunts current through the expandable member.

8. The method of claim 1, wherein applying the voltage pulse train activates the first electrode with a first polarity and the second electrode with a second polarity opposite the first polarity.

9. A method, comprising:
    transitioning an expandable member of a catheter device disposed in a vessel into an expanded configuration such that the expandable member contacts a wall of the vessel and centers a catheter shaft of the catheter device in the vessel, the catheter device including a plurality of electrodes including a first set of one or more electrodes positioned proximal to the expandable member and a second set of one or more electrodes positioned distal to the expandable member;
    receive blood into a pathway that extends through the expandable member, the pathway defined by a first opening disposed proximal to the expandable member, a second opening disposed distal to the expandable member, and a lumen extending through the catheter shaft between the first and second openings;
    applying a voltage pulse train to at least one first electrode selected from the first set of electrodes positioned proximal to the expandable member and at least one second electrode selected from the second set of electrodes positioned distal to the expandable member, such that the at least one first electrode and the at least one second electrode collectively generate an electric field for ablating tissue surrounding the vessel via irreversible electroporation; and
    passing, while applying the voltage pulse train, electric current between a proximal side of the expandable member and a distal side of the expandable member via the pathway;
    wherein at least one of the first and second set of electrodes includes electrically conductive portions that are (1) disposed below an outer surface of the catheter shaft in a recess and (2) separated by an electrical insulator disposed in the channel recess.

10. The method of claim 9, wherein the at least one first electrode and the at least one second electrode are each coupled to a different insulated electrical lead including an insulation layer having a thickness and a dielectric strength configured to withstand a voltage of at least about 2000 Volts without dielectric breakdown.

11. The method of claim 9, wherein the vessel is a renal artery, and the electric field causes renal denervation.

12. The method of claim 9, wherein the at least one first electrode is positioned between the first opening and the expandable member, and the at least one second electrode is positioned between the second opening and the expandable member.

13. The method of claim 9, further comprising recording impedance data using at least one electrode pair from the plurality of electrodes.

\* \* \* \* \*